(12) United States Patent
Horovitz et al.

(10) Patent No.: US 8,201,992 B2
(45) Date of Patent: Jun. 19, 2012

(54) SENSOR DEVICE AND METHOD FOR QUALITATIVE AND QUANTITATIVE ANALYSIS OF GAS PHASE SUBSTANCES

(75) Inventors: Michael L. Horovitz, Savannah, GA (US); Karl F. Anderson, Lancaster, CA (US)

(73) Assignee: Sensor Tech, Inc., Savannah, GA (US)

( * ) Notice: Subject to any disclaimer, the term of this patent is extended or adjusted under 35 U.S.C. 154(b) by 381 days.

(21) Appl. No.: 11/935,928

(22) Filed: Nov. 6, 2007

(65) Prior Publication Data
US 2008/0101434 A1   May 1, 2008

Related U.S. Application Data

(63) Continuation of application No. 10/192,782, filed on Jul. 9, 2002, now Pat. No. 7,329,389.

(60) Provisional application No. 60/305,190, filed on Jul. 16, 2001, provisional application No. 60/317,129, filed on Jul. 6, 2001.

(51) Int. Cl.
*G01N 25/20* (2006.01)
*G01K 17/02* (2006.01)

(52) U.S. Cl. ............. 374/29; 374/31; 374/16; 374/185; 374/35; 422/51; 436/147; 73/25.01; 73/23.25

(58) Field of Classification Search ............. 374/29–40, 374/43–45, 10–12, 144; 422/83, 50, 68.1, 422/82.02, 88, 90, 82.01, 95–96, 151, 51, 422/109, 119, 122, 94; 436/43, 147, 149, 436/151, 152, 155, 159; 73/1.01, 23.01, 73/23.05, 23.2, 1.02, 25.01, 23.25
See application file for complete search history.

(56) References Cited

U.S. PATENT DOCUMENTS 2,751,281 A    6/1956  Cohn
2,762,568 A *  9/1956  Sullivan ..................... 431/76
(Continued)

FOREIGN PATENT DOCUMENTS
EP      00018221 A1 *  4/1980
(Continued)

OTHER PUBLICATIONS

Anderson, "Your Successor to the Wheatstone Bridge? NASA's Anderson Loop" IEEE Instrumentation and Measurement Magazine, 1998, vol. 1, No. 1, pp. 5-15.

(Continued)

*Primary Examiner* — Gail Verbitsky
(74) *Attorney, Agent, or Firm* — Johnson, Marcou & Isaacs, LLC; James D. Johnson; F. Brent Nix

(57) ABSTRACT

New sensors and methods for qualitative and quantitative analysis of multiple gaseous substances simultaneously with both high selectivity and high sensitivity are provided. The new sensors rely on a characteristic difference in energy between the interaction of a particular substance with a catalyst coated heat transfer device (HTD) and a non-catalyst coated (or one coated with a different catalyst) reference HTD. Molecular detection is achieved by an exothermic or endothermic chemical or physical reaction between the catalytic surface of the sensor and the molecule, tending to induce a temperature change of the sensor. Both high temperature and non-destructive low temperature detection are possible. The magnitude and rate of endothermic or exothermic heat transfer from a specific molecule-catalyst interaction is related to molecular concentration.

9 Claims, 18 Drawing Sheets

U.S. PATENT DOCUMENTS

| | | | |
|---|---|---|---|
| 3,488,155 A | | 1/1970 | Ayers |
| 3,522,010 A | * | 7/1970 | Archer .......................... 422/96 |
| 3,537,823 A | | 11/1970 | Innes |
| 3,607,084 A | | 9/1971 | Mackey et al. |
| 3,725,005 A | | 4/1973 | Innes |
| 4,045,177 A | * | 8/1977 | McNally ........................ 422/96 |
| 4,070,157 A | | 1/1978 | Iles |
| 4,169,126 A | | 9/1979 | Iles |
| 4,170,455 A | | 10/1979 | Henrie |
| 4,183,728 A | | 1/1980 | Leitzke et al. |
| 4,246,228 A | | 1/1981 | Jones et al. |
| 4,305,724 A | * | 12/1981 | Micko ........................... 436/156 |
| 4,355,056 A | | 10/1982 | Dalla Betta et al. |
| 4,432,224 A | | 2/1984 | Typpo |
| 4,453,397 A | * | 6/1984 | Ohta et al. ................... 73/23.31 |
| 4,476,706 A | | 10/1984 | Hadden et al. |
| 4,489,590 A | | 12/1984 | Hadden |
| 4,654,624 A | * | 3/1987 | Hagan et al. .................... 338/34 |
| 4,870,855 A | | 10/1989 | Shafer |
| 4,944,035 A | * | 7/1990 | Aagardl et al. ............... 702/136 |
| 4,984,446 A | * | 1/1991 | Yagawara et al. ............ 73/31.06 |
| 5,167,927 A | * | 12/1992 | Karlson .......................... 422/90 |
| 5,212,142 A | * | 5/1993 | Dettling ........................ 502/304 |
| 5,314,828 A | | 5/1994 | Dalla Betta et al. |
| 5,330,855 A | | 7/1994 | Semancik et al. |
| 5,338,515 A | * | 8/1994 | Betta et al. ....................... 422/95 |
| 5,356,756 A | | 10/1994 | Cavicchi et al. |
| 5,371,469 A | | 12/1994 | Anderson |
| 5,444,974 A | | 8/1995 | Beck et al. |
| 5,451,371 A | * | 9/1995 | Zanini-Fisher et al. ........ 422/51 |
| 5,464,966 A | | 11/1995 | Gaitan et al. |
| 5,481,199 A | | 1/1996 | Anderson |
| 5,486,336 A | | 1/1996 | Dalla Betta et al. |
| 5,560,200 A | | 10/1996 | Maus et al. |
| 5,616,850 A | | 4/1997 | Sage |
| 5,624,640 A | | 4/1997 | Potthast et al. |
| 5,705,129 A | | 1/1998 | Takahashi et al. |
| 5,736,104 A | | 4/1998 | Oh et al. |
| 5,779,980 A | | 7/1998 | Hatfield |
| 5,795,545 A | * | 8/1998 | Koripella et al. ............... 422/94 |
| 5,813,764 A | * | 9/1998 | Visser et al. ..................... 374/12 |
| 5,858,306 A | | 1/1999 | Oh et al. |
| 5,863,803 A | | 1/1999 | Zanini-Fisher et al. |
| 5,922,287 A | | 7/1999 | Kato et al. |
| 5,923,421 A | | 7/1999 | Rajic et al. |
| 5,977,782 A | * | 11/1999 | Kordecki ...................... 324/700 |
| 5,989,398 A | | 11/1999 | Young et al. |
| 6,037,183 A | * | 3/2000 | Faber et al. ................... 436/137 |
| 6,060,025 A | | 5/2000 | Pasquariello et al. |
| 6,071,476 A | * | 6/2000 | Young et al. ..................... 422/51 |
| 6,095,681 A | | 8/2000 | Kunt et al. |
| 6,202,467 B1 | | 3/2001 | Anatolievich et al. |
| 6,238,085 B1 | * | 5/2001 | Higashi et al. .................. 374/10 |
| 6,242,263 B1 | | 6/2001 | Faber et al. |
| 6,344,173 B1 | * | 2/2002 | Faber et al. ..................... 422/94 |
| 6,550,310 B1 | * | 4/2003 | Liu et al. ...................... 73/31.05 |
| 6,635,161 B2 | * | 10/2003 | Inagaki ......................... 204/425 |
| 6,763,309 B2 | * | 7/2004 | Kieken et al. ..................... 506/8 |

FOREIGN PATENT DOCUMENTS

| | | | | |
|---|---|---|---|---|
| EP | 0819935 | | 1/1998 | |
| GB | 1105046 | | 3/1968 | |
| GB | 2238617 | | 5/1991 | |
| JP | 58115355 A | * | 7/1983 | |
| JP | 63210760 A | * | 9/1988 | |
| JP | 01265149 | | 10/1989 | |
| JP | 06501545 | | 2/1994 | |
| JP | 06242050 | | 9/1994 | |
| JP | 08285807 A | * | 11/1996 | |
| WO | WO 91/19971 | | 12/1991 | |
| WO | WO 00/40953 | | 7/2000 | |

OTHER PUBLICATIONS

Ding et al., "Surface State Trapping Models for SnO2-based Microhotplate Sensors" Sensors and Actuators, B 77, 2001, pp. 597-613.

Gall, "The Si-planar-pellistor Array, a Detection Unit for Combustible Gases," Sensors and Actuators B, Elsevier Sequoia S.A., Lausanne, CH, vol. B16, No. 1/3, Oct. 1, 1993, pp. 260-264, XP000411353 ISSN: 0925-4005.

Kunt et al., "Optimization of Temperature Programmed Sensing for Gas Identification Using Micro-Hotplate Sensors," Sensors and Actuators, B 53, 1998, pp. 24-43.

Semancik et al., "Microhotplate Platforms for Chemical Sensor Research," Sensors and Actuators, B 77, 2001, pp. 579-591.

Japanese Office Action with comments by Foreign Associate cited in Appl. No. 2003-514224, pp. 1-5, Mar. 25, 2008.

EPO Exam Report—Application No. 02752230.9, pp. 1-2, May 14, 2007.

EPO Search Report issued in 02752230.9, pp. 1-4, Feb. 26, 2005.

EPO Exam Report cited in Appl. No. 02752230.9, pp. 1-5, Oct. 29, 2009.

PCT International Preliminary Examination Report issued in Appl. No. PCT/US02/21678, pp. 1-4, Aug. 21, 2003.

Canadian Office Action cited in Appl. No. 2,543,820, pp. 1-3, Jan. 21, 2010.

Australian Patent Office—Examiner's First Report, p. 1, Jun. 26, 2008.

USPTO Office Action cited in U.S. Appl. No. 10/192,782, pp. 1-7, Jun. 27, 2005.

USPTO Office Action cited U.S. Appl. No. 10/192,782, pp. 1-5, Dec. 28, 2005.

USPTO Office Action cited in U.S. Appl. No. 10/192,782, pp. 1-5, Jul. 21, 2006.

USPTO Office Action cited in U.S. Appl. No. 10/192,782, pp. 1-5, Dec. 1, 2006.

* cited by examiner

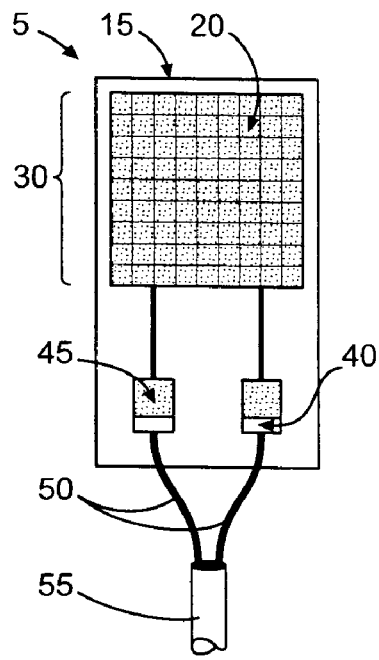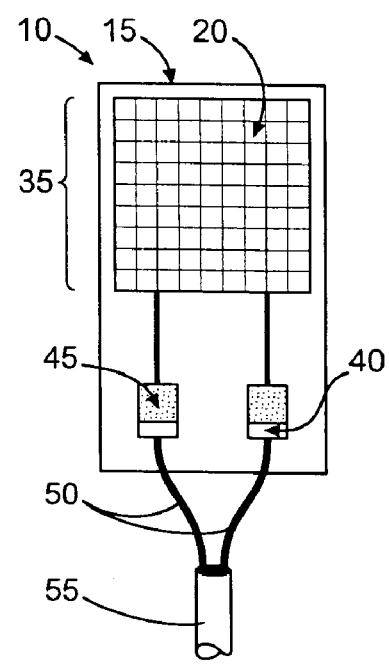
FIG. 1A  FIG. 1B
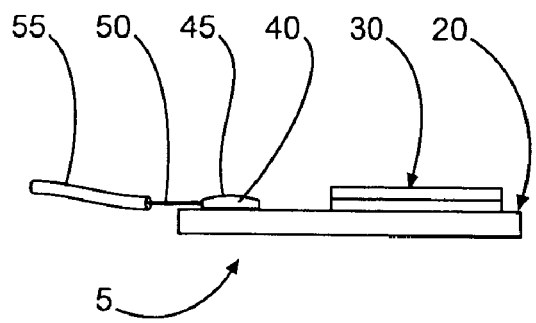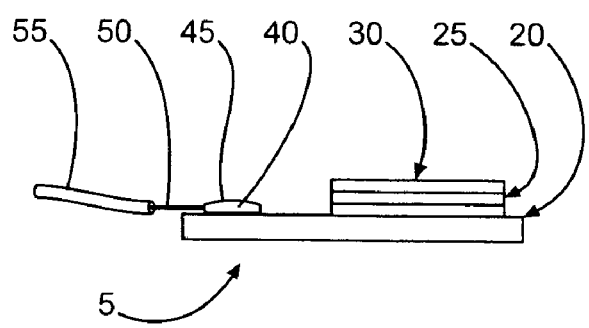
FIG. 2A  FIG. 2B

SENSOR DEVICE AND METHOD FOR QUALITATIVE AND QUANTITATIVE ANALYSIS OF GAS PHASE SUBSTANCES

PRIOR RELATED U.S. APPLICATION DATA

The present application is a continuation of U.S. patent application Ser. No. 10/192,782 filed Jul. 9, 2002, now U.S. Pat. No. 7,329,389, which claims the benefit of priority to U.S. Provisional Patent Application No. 60/305,190, filed Jul. 16, 2001, and U.S. Provisional Patent Application No. 60/317,129 filed Sep. 6, 2001, which are incorporated herein by reference.

TECHNICAL FIELD OF THE INVENTION

The present invention provides new sensors and methods for detecting, identifying, and quantifying multiple gaseous substances simultaneously and selectively. This invention is applicable to any substance that can be induced to form a gas phase molecule or material, whether that substance is a gas under ambient conditions, a liquid that can be vaporized, or a solid that can be sublimed. Further, this device provides for the discrimination of a single molecular species while ignoring others, making it particularly useful in numerous analytical, medical, environmental, safety, and security applications where both sensitivity and selectivity are required.

BACKGROUND OF THE INVENTION

Despite recent advances, there remains a tremendous need for better detection methods for measuring gas phase molecules and substances. Measurement techniques exhibiting greater reliability, reproducibility, and sensitivity are desired, particularly if they can be achieved using cost-effective sensors. For example, some analytical situations require high sensitivity devices to monitor low concentrations of volatile substances that may indicate the presence of toxic, explosive, corrosive, combustible, or otherwise dangerous materials. Other situations demand methods of high selectivity to determine the presence of a single molecular species in medical, environmental, engineering applications, without interference from other molecules. More often than not, both enhanced sensitivity and selectivity are preferred to provide the most useful and timely analytical information.

Numerous technical applications currently using standard analytical methods for trace organic and inorganic gases would benefit significantly from enhanced detection means. For example, environmental protection applications such as emissions testing, EPA compliance studies, or chemical analyses of effluent streams, require more selective and sensitive measurement techniques. More rugged and reliable field sensors that provide improved sensitivity, yet are sufficiently inexpensive and portable for routine use, would be particularly useful.

Diagnostic medical applications also require better detection methods, where certain volatile compounds indicative of a particular medical condition must be measured. For example, compounds or their byproducts indicative of a medical condition can be exuded in low concentration through the skin, from wounds, in perspiration, or occur in the breath, and therefore require reliable and highly sensitive analytical techniques for their measurement. An improved sensor is also needed for monitoring the concentration of anesthetics, or their metabolic breakdown products, as they emanate from the skin of a patient under anesthesia.

More convenient, rapid and accurate detection methods are also needed to test for the presence of alcohol, drugs, or drug byproducts in the breath of a motorist or an athlete. Such methods would be especially useful to test truck drivers, bus drivers, train engineers, ship and barge captains, and heavy equipment operators, where liability issues arise.

Improved analytical techniques are urgently needed in security applications such as airport screening and the protection of government buildings, where explosive substances can be detected by the presence of diagnostic volatile compounds. These applications are in dire need of reproducible, sensitive, and cost-effective methods for molecular detection. Home and work place security applications, where gas detection is related to both comfort and safety, have similar requirements. Similarly, suspicious areas in which land mines may occur might be identified, and mines located, through detecting diagnostic volatile compounds.

Rapid and reliable security methods are urgently needed at ports of entry to monitor the massive volume of container traffic that enters these ports in ships or across borders on trucks. It is highly desirable that every container entering the country be subject to analytical tests capable of detecting explosives, dangerous materials, or precursors to harmful substances. What is therefore needed is a test for the presence of diagnostic volatile compounds indicative of these materials, rapid enough to afford the high throughput required to test every single container.

Continuous ambient air monitoring in electronics manufacturing and storage facilities also requires enhanced analytical methods, where maintaining the integrity of the atmosphere requires a rapid and selective means of detecting contaminants in the air. Air quality control is especially important in the electronics industry to prevent damage to sensitive electronic components stored within the confines of a manufacturing facility, where the ambient air may contain harmful levels of vapors produced or used in that facility. One aspect of the electronics industry where monitoring corrosion is critical is the manufacture of magnetic recording data storage systems such as disk drives.

Air quality monitoring in archival repositories also requires improved detection methods and devices. Accurate air quality measurements must be implemented along with rigorous air purification to insure proper storage conditions for sensitive materials such as archival documents, films, photographs, lithographs, historic books and manuscripts, maps, and the like.

Further, there is a great need to protect personnel in government buildings, embassies, defense command and control areas, and even temporary field operations, against chemical or biological warfare agents, particularly during war or terrorist attacks. A technique that could be adapted to determine the presence of either chemical or biological agents, or both simultaneously, would be especially useful.

Currently, detection and measurement of volatile substances is performed by any number of methods, all of which suffer from various limitations in sensitivity, selectivity, ease of operation, or cost-effectiveness. For example, combustion-type molecular detectors currently in use employ a catalyst coating bound directly to a resistive wire, for example, alumina-supported platinum metals such as Pt, Pd or Rh on a platinum wire, which is heated up to several hundred degrees Celsius. When the heated catalyst contacts the target gas, the heat of combustion increases the temperature of the platinum wire, which is detected as a voltage change, resulting from a change of the electrical resistance of the wire in response to the temperature increase. However, correct measurements are difficult, due in part to the difficulty in accurately quantifying a comparatively small temperature increase (ΔT) at a high temperature (T). Further, the resistive wire is prone to electromagnetic interference and is subject to physical movement and turbulence within the air stream, resulting in signal noise. Chemical poisoning of the supported metals may also result in unreliable results.

A related type of sensor for gas phase molecules in common use is the resistance-type sensors utilizing a metal oxide, especially an n-type semiconductor oxide such as $SnO_2$, and often supported on ceramic beads. These detectors operate on the basis of catalytic oxidation of a target molecule by adsorbed oxygen, with a concomitant reduction of the semiconductor oxide, and are often used for measuring the combustible hydrocarbons or CO in automobile exhaust. The change in resistance of the sensing element resulting from oxygen desorption, upon oxidation of the combustible gas, is used as a proxy for gas concentration. However, presently available sensors are susceptible to numerous interfering compounds such as such as alcohols, humidity, Si-containing compounds, other volatile organic compounds, and even varying oxygen levels, resulting in inaccurate and non-reproducible results. Chemical poisoning of the $SnO_2$ may also be problematic. Further, the resistance of the semiconductor itself varies at high temperatures, further rendering the results unreliable.

Some gas sensors are designed to detect a specific type of gaseous molecule only, and therefore are not generally applicable. For example, one type of detector relies on a proton-conductive layer which functions to dissociate and thereby detect, hydrogen or other proton-releasing molecules. However, such a detector is adapted only for measuring proton-releasing molecules. Similarly, some air-fuel ratio sensors that detect $O_2$ use an oxygen ion conductive solid electrolyte detector. This device is adapted only for measuring molecules that form oxygen ions upon contact with the electrolyte. Moreover, such detectors typically require very high operating temperatures (up to about 700° C.).

Some gas detectors are based on very explicit chemical reactions or specific spectroscopic properties of the target molecule, as in the case of some conventional $NO_x$ analyzers. For example, detection may be accomplished by chemical luminescence or by gas-phase infrared or Raman spectral analysis of various vibrational chromophores of a target molecule. Such methods are typically not readily adapted for directly situating the detecting element into a fluid stream, and therefore are not suitable for analyzing transient gas concentrations, a needed capability when combining detection with electronic controls, such as in automobile emissions systems under feedback control. These systems may also require frequent maintenance of optical components, further reducing their utility.

Other devices used for the identification of molecular contaminants rely on simple changes in the thermal conductivity of the gas being examined. However, thermal conductivity is a macroscale measurement that evaluates any mixture of gases with which the detector is presented. Such devices are not capable of discriminating among discrete molecules, but rather provide qualitative rather than quantitative measurements. As a result, their utility is severely limited and would not, for example, be able to distinguish the thermal conductivity component of a single gas such as a single metabolic gas or a single component in cigarette smoke.

Fuel cell technologies have also been utilized in the detection of specific molecules, particularly when the target appears in low concentrations. However, this technique is often ineffective because the chemical reaction driving the fuel cell reaction can be nondiscriminatory, compromising the ability of this method to distinguish among multiple molecular species.

It has therefore become imperative to address the present limitations associated with gas phase molecular detection by providing new devices and new methods for detecting, identifying, and quantifying gaseous substances. The new systems would preferably utilize a fundamentally new method of detection that affords enhanced selectivity, while retaining the necessary sensitivity. The present invention addresses these problems by providing novel sensors and methods for selectively identifying and measuring gaseous substances. The new sensors achieve high sensitivities, allowing the detection of gas phase species at very low concentrations, and greatly expanding their applicability. The new sensors are also highly selective, able to distinguish a single molecular species while ignoring all others. This capability which makes this invention especially useful in critical analytical areas such as security and medical applications. This improved selectivity results in highly reliable measurements and significantly reduces the cross-sensitivity from interfering species. This invention also provides new analytical paradigms for detecting and measuring multiple target substances simultaneously and with high reproducibility. Further, the sensors and methods of this invention are relatively simple as compared to many of the current technologies, thereby providing a more error-free operation and significantly greater cost-effectiveness in return.

SUMMARY OF THE INVENTION

The present invention addresses many of the current limitations in gas phase molecular detection of trace organic and inorganic species, by providing new sensors and methods that achieve high sensitivity, selectivity, reliability, and cost-effectiveness. Because the new sensors rely on a characteristic energy associated with a particular molecule, whether a bond energy, adsorption/desorption energy, or reaction energy of some type, the sensors are capable of discriminating qualitatively among a large number of molecules.

Typically, a sensor of the present invention includes a thin catalyst coating which is in thermal contact with the outer surface of a heat transfer device HTD. The HTD receives heat from and delivers heat to its environment in a manner that can be observed and measured as temperature change or as the flow of thermal power. Typically, the HTD is brought to its operational temperature by electrical self-heating that takes place in a resistance temperature detecting device. Thus, the resistance temperature detector (RTD) serves the dual purpose of a non-catalytic heating means and a temperature detecting means. Typically, the catalyst-coated, heated HTD is situated in the interior of a passage such as a tube, through which the flow rate of the contaminated gas stream over the detector is controlled and measured. In a typical embodiment, a reference detector consisting of a heated HTD without the catalyst coating, is placed proximate to the heated catalyst-coated HTD sensor such that the sensor and reference detectors contact the same gas stream.

The operational concept of this sensor is summarized as follows. When a sample gas is brought in contact with a catalyst-coated, sensing HTD element at the proper temperature, some type of chemical or physical interaction can occur. A (non-catalytic) heat source is used to heat the catalyst surface to an appropriate reaction temperature, usually greater than ambient, therefore the HTD includes a variable resistance heater (VRH) which serves both as a non-catalytic heating function and as a temperature sensing means. Regardless of the type of molecule-catalyst interaction, there is some enthalpy change associated with this interaction, therefore any reactivity or adsorption process induces additional "catalytic" heat flow between the catalyst surface and the body of the sensing HTD. This activity will increase the temperature of the sensing HTD if the process is exothermic and decrease the temperature of the sensing HTD if the process is endothermic. A reference HTD in substantially the same environment would respond only to the non-catalytic heat energy transfer because it does not have a catalytic surface. By electronically comparing the difference in the heat transfer at the reference and sensor HTD elements, a sample gas may be detected and quantified.

In general terms, there are two primary measurement strategies by which the physical and chemical reactivity at the catalyst surface is detected and measured (offset and null-balance), various feedback control approaches for establishing non-catalytic heat input levels, and two measurement approaches (single-ended, sometimes called 'single,' and differential), and a measured parameter may be a direct observation or derived from two or more individual measured parameters. The preferred measurement strategy, control approach for non-catalytic heat, measurement approach and parameters measured will obviously vary with the specific requirements of a particular application.

Either an offset (temperature change) or a null-balance (power change to maintain substantially the desired instantaneous temperature) measurement strategy may be employed to estimate the change in a sensor HTD's total heat energy flow (power) caused by catalytic heat energy flow adding to—or subtracting from—the non-catalytic heat energy flow which was used to bring the HTD to its operational temperature. The null-balance measurement strategy is employed when the heat energy transfer required to hold the HTD at a desired temperature is observed as an indication of thermodynamic activity. Therefore, a null-balance measures how much power is required to maintain the sensing HTD at its initial temperature, prior to the onset of reaction. The offset measurement strategy is typically employed when the temperature difference between two (or more) HTDs is observed as an indication of thermodynamic activity. Therefore, an offset measurement determines heat transfer from the change in temperature of the sensing HTD from its initial temperature, prior to the onset of reaction. While the apparatus required to accomplish an offset measurement tends to be simpler, it is more typical to employ the null-balance strategy in order to more thoroughly identify the thermodynamics that result from reactivity or catalytic activity.

Molecular detection using the present invention can be achieved by observing either an exothermic or endothermic chemical or physical reaction between the catalytic surface of the sensor and the molecule, a reaction that induces a heat exchange at the sensor. The magnitude and rate of endothermic or exothermic heat transfer from a specific molecule-catalyst interaction is related to molecular concentration. It is not necessary to identify that exact reaction that ensues or the particular stoichiometry involved for any unique temperature/molecule/catalyst combination, in order to use the simple observation of the heat of that reaction in a qualitative and quantitative manner.

Generally, there are three operational modes by which a detector of this invention can be driven, an isothermal (constant temperature) mode, a calorimetric spectroscopy (variable temperature) mode, and a mixed mode (constant sensor HTD temperature with varying reference temperature). Molecular detection is based on a discrete, characteristic reaction energy associated with a molecule of interest in contact with a particular catalyst, at a predetermined temperature, that is, a unique molecule/temperature/catalyst combination.

In the isothermal mode, the specific operating temperature is experimentally determined for the individual target species to be detected, and for the specific catalyst which induces a reaction of that target species. The detector is activated by passing an electrical current through the reference and the sensor VRH elements. When no reaction is occurring at the sensor, and the reference and the sensor are at the same temperature, there is essentially no difference in the voltage drop across the substantially identical reference and the sensor VRH elements.

The monitoring signal may be expressed in convenient units such as voltage or power. When even a minute temperature change occurs at the sensor, its electrical resistance changes, and the resulting voltage difference between the sensor and the reference is readily detected. Typically current through the sensor VRH is then increased or decreased, depending upon the exo- or endothermicity of the process, to maintain substantially the desired instantaneous temperature, the magnitude of which is related to molecular concentration. Thus, current is increased for endothermic processes and decreased for exothermic processes, thereby maintaining the total (catalytic plus non-catalytic) heat input constant to a sensor HTD. Selectivity among different molecules is possible because there is a unique combination of catalyst identity and temperature (which is maintained at substantially the desired instantaneous temperature through applied current) that results in a particular reaction of the molecule of interest.

If the offset measurement strategy is employed, then the temperature difference between a sensor HTD and a reference HTD is allowed to vary, and both the direction and magnitude of this temperature difference is observed as a measure of catalytic activity. There are several alternatives available for regulating the power input to the non-catalytic heat source, the VRH, of the sensor HTD. These alternatives include, but are not limited to control of the voltage across the VRH, control of the current through the VRH and control of the resistance of the VRH. Of these alternatives, control of the resistance of the VRH results in maintaining the temperature of an HTD at the preferred level.

If the null-balance measurement strategy is employed then the temperature of sensor and reference HTDs are held at substantially the same temperature by their individual closed-loop control means. In this strategy, the difference in electrical (non-catalytic) power supplied to their VRH elements is observed as a measure of catalytic activity.

The reaction that occurs between catalyst surface and gas-phase molecule is often an oxidation of the molecule being detected that results in bond-making and bond-breaking processes. However in principle, any type of chemical or physical reaction such as adsorption and/or desorption at lower temperatures may be used to detect the presence of a particular molecule. The new sensor is capable of providing both qualitative and quantitative measurements of gas-phase molecules. Heat flow and the resulting electrical response is directly proportional to concentration, therefore by using concentration standards, quantitative measurements of any particular gas are readily attainable.

The HTD sensor assembly is typically placed in the interior of a high temperature-resistant transducer tube, which allows the molecules to be brought into contact with the HTD assembly by a flow of gas produced by a small vacuum pump placed downstream of the gas flow. This embodiment allows for gas samples to be collected in close proximity to the detector assembly and remotely from the electronics components, and readily permits continual monitoring of a gas stream. Further, when the sensor contacts a moving fluid stream during the course of a measurement, the sensor encounters a relatively constant concentration of the target molecule for that flow rate, therefore the magnitude and temperature of the signal is unique to a given flow rate. While this arrangement it typical, the sensor can also operated under static air conditions, in which case molecular detection is presumed to be diffusion controlled. This detector can also be adapted to detect substances that can be put into the gas phase, namely liquids that can be vaporized or solids that can be sublimed. Further this detector could conceivably be placed in a liquid stream for detecting solution-borne, especially water-borne, contaminants, as well as detection of airborne pathogens due to specific surface elements interacting with a catalyst. HTD sensors with different coatings can be placed in series or in parallel with the flow of sample gas to detect additional molecules that have different types and classes of functional groups and/or different reaction temperatures. Various coatings may be used as a catalyst on the HTD, but typically the coating contains a metal oxide. Often, the typical catalyst coating is a first row, transition metal oxide.

The calorimetric spectroscopic, or variable temperature mode of operating the detector of this invention involves the variation of detector temperature in a predetermined manner, usually by continuously cycling a programmed temperature vs. time profile. Qualitative and quantitative measurements of multiple target molecules are achieved by operating the detector in this calorimetric spectroscopy mode, that is by continuously monitoring the calorimetric response associated with each temperature over the range of temperature variation. This method provides a collection of unique temperature/molecule/catalyst combination data points in which specific molecules are characterized by specific patterns of calorimetric response vs. temperature. Significantly, this dynamic temperature mode may be operated using multiple sensors in the detector apparatus, each with a different catalyst coating and operating at substantially the same instantaneous temperature or the same coating using a different catalyst surface topology. Separate and substantially identical temperature control and monitoring electronics operate each sensor and observe their calorimetric response as temperature is cyclically and synchronously varied. Multiple target molecules may be qualitatively and quantitatively analyzed simultaneously using this calorimetric spectroscopy method by gathering multi-dimensional data sets through the temperature cycling program. This method thereby achieves the simultaneous determination of the presence and concentration of multiple target molecules in near real time. Standard multi-dimensional correlation techniques routinely used for pattern recognition and image processing are adapted to refer to pre-stored patterns which are used to compare and identify patterns in the data characteristic of the calorimetric response of the various catalysts to specific molecules.

Importantly, the sensor of the present invention has the capability to provide specific qualitative and quantitative molecular detection at temperatures substantially lower than those needed for typical chemical reactions. It is therefore not necessary to operate this sensor at temperatures high enough for covalent bond-breaking and bond-making to ensue. This sensor is capable of probing the unique, low energy adsorption or desorption reaction energies between a target molecule and the catalyst-coated HTD surface, at a specified temperature. For example, the energy necessary to desorb a given molecule from a given surface at a specific temperature is unique, and a temperature vs. energy profile can identify the molecule and its concentration to the exclusion of other molecular species. In addition to simple adsorption and desorption, other low temperature phenomena may be used for specific qualitative and quantitative molecular detection information, such as hydrogen-bond formation and dissociation, and the study of catalyst conduction bands. Thus, the uniqueness of the temperature vs. heat flow profile is applicable to virtually any chemical or physical interaction between the target molecule and a specific surface.

Thus, the present invention provides novel methods and devices directed toward highly selective detection of molecules and substances at low concentration.

The present invention also encompasses fundamentally new ways to detect and quantify gas phase contaminants by measuring either exothermic or endothermic chemical or physical interactions between the sensor and the molecule. These interactions induce heat transfer at the sensor, which is observed by measuring the increase or decrease in electrical power needed to keep the sensor at substantially the desired instantaneous temperature, relative to a non-reacting reference.

In addition, the present invention provides HTD sensors with a range of different coatings and topologies can be placed in a series or parallel configuration to detect additional molecules that have different types and classes of functional groups, different reaction temperatures, and/or different energetics associated with interaction with the catalyst-coated HTD.

The sensor of this invention is also capable of probing the unique, low energy adsorption or desorption reaction energies between a target molecule and the catalyst-coated HTD surface at a given temperature, thereby opening up a new range of molecules that may be detected and new applications for the sensor.

Further, this invention affords rugged and reliable molecular detection sensors that are capable of significantly improved sensitivity, reproducibility, and cost-effectiveness over presently available sensors, yet are sufficiently inexpensive and portable for routine use.

Accordingly, one advantage of this invention is the measurement of very low concentrations of one or more specific target molecules in the gas phase that may be monitored by continuous sampling from the environment.

Another advantage of this invention is to provide a method of detecting and quantifying target molecules, without the need for separating non-target molecules from the sample that would provide false signals using currently available measurement approaches.

A further advantage of this invention is to provide a simple, relatively low-cost sensing and electronics apparatus that is capable of detecting and measuring the presence of a specific target molecule, thereby lowering the cost of analytical measurements, and increasing the ease with which they are obtained.

Yet another advantage of the device and methods of this invention is to obtain continuous electronic data, including that obtained from continuous ambient air monitoring, representative of both the concentration and the rate-of-change of the concentration of a specific target molecule of interest.

Another advantage of the present invention is the qualitative and quantitative analysis of multiple target molecules simultaneously using a variable temperature, or calorimetric spectroscopy, method which gathers multi-dimensional data sets through a temperature cycling program.

One other advantage of this invention is access to specific qualitative and quantitative molecular detection data at temperatures substantially lower than those needed for typical chemical reactions, namely data resulting from low energy adsorption or desorption reaction energies between a target molecule and the catalyst-coated sensor surface, at a specified temperature.

Still another advantage of this invention is the development of sensors and methods that reduce the time required to observe the change in concentration of a specific target molecule.

One additional advantage of the present invention is to provide devices and methods for obtaining a sample for analysis by operating the sampling and sensing elements of the device, i.e. the detector or probe, at a significant distance from the signal conditioning electronics. This capability allows the detector of the present invention, typically situated in a vacuum sampling tube, to be situating directly in a fluid stream, and therefore be adapted for analyzing transient gas concentrations. This capability is especially useful when combining detection with electronic devices under feedback control, such as in automobile emissions systems.

Another advantage of this invention is to provide electronic information about low concentrations and changes in concentration of specific target molecules to digital processors, for any further analysis required, and to effect any desired subsequent action thereon.

Still another advantage of this invention is the intimate thermal contact between the molecular sensing catalytic coating and the heating element of a detector, by use of a HTD located just beneath the surface of the catalytic coating, to achieve greater sensitivity, more signal strength, and more rapid response times with a minimum of circuitry interference.

Yet another advantage of this invention is the development of novel analytical techniques that can be adapted to determine the presence of chemical agents, biological agents, or both simultaneously.

Yet a further advantage of the present invention is the detecting and measuring specific target compounds in the gas phase, even in the presence of potentially interfering compounds, to determine the concentration of the target compounds with accuracy and reproducibility.

A further advantage of this invention is the reliable detection of compounds or their byproducts that might be exuded in low concentration through the skin or in the breath.

These and other features, aspects, objects and advantages of the present invention will become apparent after a review of the following detailed description of the invention.

BRIEF DESCRIPTION OF THE FIGURES

FIG. 2 illustrates cross sectional drawings of two different embodiments of catalyst-coated sensing HTDs. FIG. 2A represents a sensing HTD with a catalyst layer situated directly on the surface of the electrically resistive material, without the use of a high temperature adhesive. FIG. 2B represents a sensing HTD with a coating of high temperature resistant adhesive to which is bonded a layer of catalyst, so as to place the catalyst in thermal contact with the HTD.

FIG. 7 illustrates one embodiment of a sensor of this invention in which multiple HTD sensor assemblies are situated in parallel within a single temperature-resistant transducer tube, thereby allowing the simultaneous detection and measurement of multiple gas phase molecules of interest. This embodiment of parallel multiple detectors constitutes a radial arrangement of seven sensor elements and one reference element.

In FIGS. 9A and 9B, the RTD material is shown unsupported, though other embodiments include supporting the RTD material on a ceramic substrate which serves as a heat conductor.

In FIGS. 10A and 10B, the RTD material is shown unsupported, though other embodiments include supporting the RTD material on a ceramic substrate which serves as a heat conductor.

DETAILED DESCRIPTION OF THE INVENTION

Figure 3:
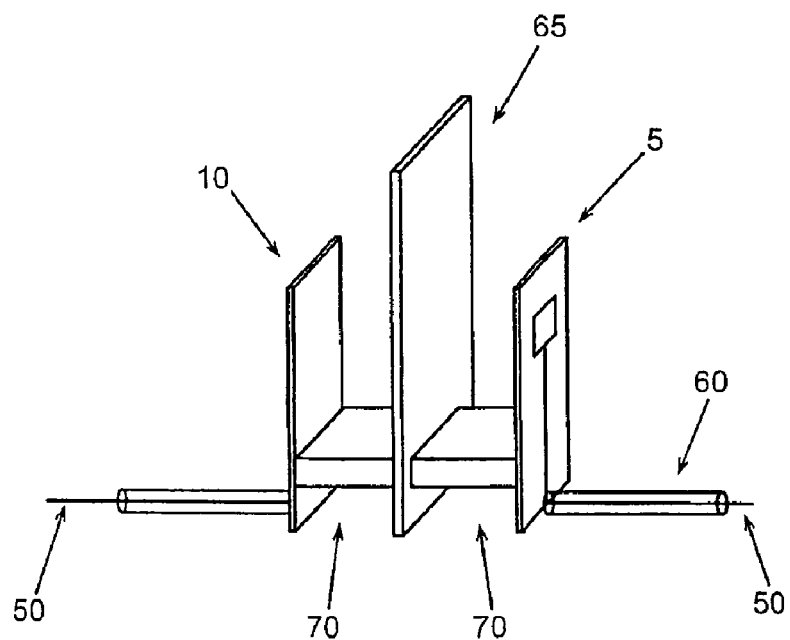
FIG. 3 illustrates one embodiment of the sensor assembly of the present invention, showing the relative orientation of the sensing HTD element, the reference HTD element, and the thermal barrier, separated by spacing means to maintain each element a certain distance from the thermal barrier.

The present invention provides new sensors and methods for detecting, identifying, and quantifying gas phase substances, including multiple gas phase substances simultaneously, particularly organic, inorganic, and organometallic molecules and pathogens present in low concentrations. Further, these new sensors and methods provide for the discrimination of a single molecular species while ignoring others, making it useful for analytical applications in numerous technical areas.

Definitions

In order to more clearly define the terms used herein, the following definitions are provided.

A heat transfer device (HTD), as used herein, refers generally to a device made of a substance with a known coefficient of heat transfer and thermal capacity which constitutes both a means for transferring heat energy to and from its thermal environment, and also provides a means for estimating the temperature of its environment or any other material in thermal contact with the HTD. There are two types of HTD elements, namely a sensing HTD and a reference HTD, therefore, this term is typically used synonymously with sensing element, detecting element, and the like, to refer to the arrangement of components that constitutes either a sensing element with a catalyst coating, or a reference element without a catalyst coating (or with a different catalyst second coating than the sensing element). The temperature of the sensing element HTD and reference element HTD are measured by a temperature observing means, typically a resistance temperature detector (RTD), in intimate thermal contact with the heat transfer means. A heating means provides non-catalytic heating to the elements typically by a variable resistance heater (VRH), and often this heater is the resistance temperature detector (RTD) itself, with sufficient electrical current flowing through it to achieve the desired operating temperature. Thus, an HTD exhibits a thermal capacity to store heat energy and a thermal resistance to the heat flow that transfers thermal energy between the various heat energy sources and sinks that constitute the HTD and the thermal environment surrounding the HTD. Often, an HTD includes a heat conductor, typically a ceramic material, in thermal contact with the VRH, which serves to, among other things, dissipate heat during the operation of the HTD.

As used herein the term variable resistance heater, or VRH, refers to a material that constitutes one component of the sensing element and the reference element, which provides a means for internally heating each element by an electrical current passing through the VRH material. As an example, a VRH can consist of a tungsten filament that is sufficiently passivated that it is not reactive upon heating in air. Each HTD component of this invention (sensing and reference) contains a VRH element. The sensing HTD contains a catalyst coating, and the reference HTD either contains no catalyst coating, or a different catalyst coating than the sensing HTD. In this way, two or more VRHs having substantially identical heat transfer characteristics are used to provide means to compare heat transfer events that occur at a first catalyst-coated VRH to a companion observation at a second VRH that is either non-catalyst-coated, or is coated with a different catalyst than the first VRH. Typically, the heating function of the VRH is carried out by the same component that serves as a temperature detector, that is by a temperature-detecting resistance wire with sufficient current passing through it to provide the required heat. Therefore in the present invention, a VRH often constitutes a resistance temperature detector (RTD) that serves the dual functions of electrical resistance heater and resistance temperature detector. In this case, this single component that combines RTD and VRH functions may be referred to as either the RTD or the VRH component.

The term resistance temperature detector, or RTD, as used herein, refers to one type of temperature indicator or detector component of the sensing element and the reference element. An RTD is typically, though not necessarily, made of a material having a positive temperature coefficient of resistance which provides a means for estimating the temperature of the individual elements. The RTD may be internally heated by an electrical current passing through its temperature-detecting resistance wire, in which case the RTD serves the dual functions of resistance temperature detector and variable resistance heater (VRH). This embodiment in which a single component combines RTD and VRH functions is typical, and may be referred to as either the RTD or the VRH component.

The term sensing element, reactive element, sensor element, sensor VRH, sensor HTD, active element, catalyst-coated HTD, catalyst-coated VRH, and related terms, as used herein, refer to the HTD component of the sensor that includes a catalyst coating attached to a temperature detector and a variable resistance heater. The catalyst coating is attached to a temperature detector by any means that will securely place the coating in substantial thermal contact with both the temperature detector and the variable resistance heater. Typically, the catalyst is adhered to the HTD with a high temperature-resistant bonding material. Thus, the portion of the sensor placed in contact with a sample gas that includes a catalytic heat source and a non-catalytic heat source is a sensor HTD. The heating element (VRH) of the sensing HTD is typically passivated by coating it with a high temperature-resistant, non-porous material that prevents the VRH material itself from reacting upon heating. For both high and low temperature embodiments, passivation materials are typically non-porous electrical insulators, which should minimize the contamination of catalytic data due to stray electrical currents which appear in the catalytic data as if there have been VRH electrical resistance changes. In some cases, the catalyst coating of the VRH sensor functions to passivate the VRH material, thereby combining the catalytic function and passivation function in a single material.

The term reference element, reference VRH, reference HTD, non-active element, uncoated or non-coated HTD, uncoated or non-coated VRH and similar terms, as used herein, refers to an HTD that either contains no catalyst coating, or in some embodiments, contains a different catalyst coating than the sensing HTD. Typically, the reference HTD includes a temperature detector and a variable resistance heater in thermal contact with the temperature detector, but without a catalyst coating. The reference HTD is usually passivated by coating it with a high temperature-resistant, non-porous material that will prevent its contact with, and reaction with, its environment. When the portion of the HTD placed in contact with a sample gas includes only a non-catalytic heat source, or in some embodiments, a different catalytic heat source as compared to the sensor VRH, the arrangement is a reference HTD.

As used herein, the terms catalyst, coating, catalyst coating, reactive coating, and the like refer generally to any substance that is placed in permanent physical and thermal contact with a HTD, and typically forms a layer thereon, to form the sensing element of the sensor assembly. The term catalyst is used whether that substance actually performs a catalytic function or not, and irrespective of the chemical composition of the substance or method of applying the substance to the HTD.

As used herein, the terms sensor, detector, detecting element, sensor assembly, detector assembly, HTD sensor assembly, VRH sensor assembly, probe, and similar terms are used to refer to the arrangement of components that contains both a sensing or reactive element with a catalyst coating (a sensor HTD), and a reference element, either without a catalyst coating, typically with a passivating coating or with a different catalyst coating than the sensing element (a reference HTD). Occasionally these same terms also include the electronics portion thereby constituting the entire device or apparatus, as the context requires.

The terms molecule, target molecule, compound, substance, gaseous substance, contaminant, and the like are used interchangeably herein to refer to any material that is the subject of detection by the sensors and methods of this invention. It typically applies to gas phase chemical species, but also refers to airborne biological materials such as viruses and bacteria, or any other material which would normally have an energy component associated with a physical or chemical interaction with the sensing (or reactive) element of the sensor, that is different from the energy component associated with a physical or chemical interaction with the reference element of the sensor.

The term signal conditioning is used herein to represent the electronic and pneumatic apparatus connected to an HTD to provide non-catalytic energy under appropriate closed-loop control to its variable-resistance heater, and to observe and report the various measurements that determine temperature, voltage, current, resistance, power, and the like.

The terms measurement, estimate and the like are used herein to represent the determination and reporting of the magnitude, direction and polarity of physical quantities such as temperature, electrical voltage, electrical current, electrical resistance, electrical power and gas flow.

The terms null-balance measurement, null-balance strategy, null-balance mode, and the like, are used herein to represent a measurement strategy employed when the amount of energy required to maintain some property of the sensor constant during an ongoing thermodynamic process is measured. Usually, the heat energy transfer required to hold the HTD at substantially a desired instantaneous temperature is observed and measured as an indication of thermodynamic activity. The required heat energy is measured relative to either the reference HTD for differential measurements, or the initial temperature of the sensing HTD for single-ended measurements. The null-balance measurement strategy has the advantages of identifying an HTD's thermodynamics in a particularly useful manner. In addition, null-balance measurements are easily obtained in both elevated temperature and low temperature ranges.

The terms offset measurement, offset strategy, offset mode, and the like, are used herein to represent a measurement strategy employed when some property of a sensor or reference device is monitored, and how far that property is displaced from its original value during an ongoing thermodynamic process is measured. Usually a change in temperature due to catalytic activity at the sensor HTD, either relative to the temperature of the reference HTD for differential measurements, or relative to the initial temperature of the sensing HTD for single-ended measurements, are observed. The offset measurement strategy typically has the advantage of simplicity and the disadvantage of the sensor and reference HTDs necessarily operating at different temperatures.

Regardless of whether a null-balance measurement strategy or an offset measurement strategy is used, the electronic output may be either a single measurement or a differential measurement, defined as follows.

The terms single measurement, single-ended measurement, single channel measurement, single channel mode and the like are used to represent an actual measurement made when there exists some common element, condition or reference level against which that property is measured. For example, voltage can be measured against a simple ground or common ground reference. When the temperature of and/or non-catalytic power to a single sensor HTD is observed to estimate the flow of heat energy between the sensor HTD and its environment, the observation is termed a single or single channel measurement. A single measurement involving only a sensor HTD will include a systematic error due to the uncertainty from variations in the HTD's thermal environment. Systematic errors can typically be minimized by corrections with measurements using a sample gas known not to contain the target molecule, however in many cases, it is preferred to use differential measurements to avoid these necessary corrections.

The terms differential measurement, differential mode, dual channel measurement, and the like are used to represent an actual measurement in which a property difference, for example a voltage difference, between two floating points is observed, where neither voltage measurement is individually referenced to a common signal potential. When the temperature difference and/or non-catalytic power difference applied to two or more HTDs is observed to estimate the difference in the flow of heat energy between these HTDs and their substantially identical environment, the observation is termed differential measurement. Differential measurements between one or more sensor HTDs and at least one reference HTD are more typical and usually preferred over a single measurements to avoid uncertainties from variations in an HTD's thermal environment, and to avoid corrections.

The term 4-wire measurement, Kelvin measurement, Kelvin arrangement, Kelvin measurement circuit topology, and the like, all refer to the classic circuit topology employing four wires for measurement of the electrical potential or voltage difference across an electrical resistance. This topology is described in IEEE Instrumentation & Measurement Magazine 1998, vol. 1 (no. 1), pages 6-15, which is incorporated herein in its entirety by reference. Kelvin measurements provide an electrical output as a either a single-ended or a differential measurement. A Kelvin measurement output virtually eliminates any uncertainties in voltage drop or resistance change across the lead wire, and makes this arrangement especially utilitarian in operating the detector portion of the sensor a significant distance from the electronics portion of the sensor.

The term thermal resistance is defined as the ratio of the temperature difference between regions within the HTD and between the HTD and its surrounding region to the heat energy flow rate between these regions.

The term thermal capacity is defined as the ratio of temperature change to the quantity of heat energy change in regions within the HTD.

The terms constant temperature mode or isothermal mode of operating the present invention refers to a method of operating a sensing and reference element at essentially one temperature, for the purpose of detecting a single substance. Because molecular detection is based on a discrete, characteristic reaction energy associated with a molecule of interest in contact with a particular catalyst at a predetermined temperature, there is typically a unique combination of target molecule/temperature/catalyst that is experimentally determined for the individual target species to be detected, and for the specific catalyst which induces some reaction of that target species. For a given target species, a library of possible catalysts and detection temperatures can be determined, regardless of the type of reaction (oxidation, reduction, adsorption, desorption, and the like) is involved with detecting the species.

The terms calorimetric spectroscopy mode, variable temperature mode, dynamic temperature mode, dynamic mode of operating the present invention refers to a method of operating the detector by varying the detector temperature (both sensing and reference elements) in a predetermined manner, usually by continuously cycling a programmed temperature vs. time profile, for the purpose of detecting a multiple substances in a gaseous sample. By continuously monitoring the calorimetric response associated with each discrete temperature over the range of temperature variation, both qualitative and quantitative measurements of multiple target molecules are achieved. This dynamic temperature mode is typically, but not necessarily, operated using multiple sensors in the detector apparatus, each with a different catalyst coating and operating at substantially the same instantaneous temperature.

Description of the Heat Transfer Device (HTD) Detector Assembly and Its Operation The sensor assembly of the present invention is an arrangement of two principal elements or portions, namely a sensing or reactive element and a reference element. The entire sensing apparatus includes the signal conditioning electronics.

The HTD sensing element of the sensor consists of a catalyst coating that is anchored to the surface of the HTD by any means that will securely place the coating in substantial thermal contact with the HTD, yet can withstand high temperatures that may be encountered during its operation. For example, a high temperature-resistant adhesive or simple physical sputtering of the coating onto the HTD may be used to adhere the coating to the HTD. Any preference in technique would arise from convenience and cost considerations, as well as the amenability of the coating to the particular technique (such as sputtering), as readily determined by one of ordinary skill in the art. The coating is typically applied uniformly such that a constant thickness of approximately three to ten microns (3-10 µm) is obtained across the entire coated surface. Coatings of somewhat more or less thickness may be applied, however this typical depth is sufficiently thin to present minimal heat flow interference. Thus, a thickness of 3-10 µm is typical to allow for maximum sensitivity of the sensing element, without obstructing heat flow.

The coating composition on the HTD that may serve as a catalyst constitutes, among other things: 1) a metal oxide of varying topologies; 2) a metal-"non-oxide" element composition such as a metal boride, carbide, silicide, nitride, phosphide, arsenide, sulfide, selenide, telluride, halide (fluoride, chloride, bromide, or iodide), and the like; 3) a complex inorganic substance in which more than one metal is combined with an element (e.g. a bimetallic sulfide); 4) a complex inorganic substance in which a metal is combined with more than one other element, e.g. a metal oxycarbide; 5) a metal; 6) other binary or ternary compounds that combine non-metals with non-metals, such as boron nitride, or combine metals and metals, such as a bimetallic alloy; or 7) combinations or mixtures thereof. Thus, the coating composition may consist of a "mixed oxide" compound such as $BaTiO_3$ or $YMnO_3$, which is a single chemical phase with more than one metal combined with oxygen to form a single compound. However, the coating composition may also encompass simple mixtures of two oxide compounds, of which an $In_2O_3/SnO_2$ mixture is an example. The metal contained in any of these components can either be a transition metal (such as manganese, iron, cobalt, nickel, copper, or molybdenum) or a non-transition, "main group" metal (such as tin, indium, or gallium). The catalyst may also constitute an organic or an organometallic substance that can be situated in thermal contact with the HTD, yet can withstand temperatures sufficient for the sensor to operate. The catalyst can be a doped semiconductor.

Typically, the catalytic coating on the HTD is a metal oxide. In particular, catalysts that can be used in this invention include, but are not limited to, all d-block, transition metal oxides in virtually any oxidation state, mixed-valent oxides, mixed-metal oxides, and combinations of oxides. Examples of metal oxide catalysts that can be used include, but are not limited to, the catalysts shown in Table 1. The oxide itself may be anchored to the surface of the HTD sensor, or an oxide precursor such as the pure metal may be attached to the HTD sensor, and converted into the oxide catalyst. For example, copper may be deposited on the sensor, and heated in air to effect conversion of copper to copper oxide. In addition to the oxides shown in Table 1, oxides of zirconium, hafnium, niobium, tantalum, tungsten, osmium, rhenium, or combinations thereof are also useful in this invention.

TABLE 1

Examples of some oxide catalysts for the present invention.

| Metal Oxide | Catalyst Formulas |
|---|---|
| Scandium oxide | $Sc_2O_3$ |
| Titanium oxide | $TiO_2$ |
| Zinc oxide | $ZnO$ |
| Vanadium oxide | $V_2O_5$, $V_2O_3$ |
| Nickel oxide | $NiO$ |
| Manganese oxide | $MnO$, $Mn_2O_3$, $MnO_2$ |
| Iron oxide | $Fe_2O_3$ |
| Copper oxide | $CuO$ |
| Chromium oxide | $Cr_2O_3$ |
| Cobalt oxide | $Co_3O_4$ |
| Molybdenum oxide | $MoO_2$ |
| Aluminum oxide | $Al_2O_3$ |
| Tin oxide | $SnO_2$ |
| Ruthenium oxide | $RuO_2$ |
| Rhodium oxide | $Rh_2O_3$ |
| Palladium oxide | $PdO$ |
| Silver oxide | $AgO$ |
| Iridium oxide | $IrO_2$ |
| Platinum oxide | $PtO_2$ |

The catalyst can be qualitatively selected for a molecule in the high temperature mode for the first row transition metals oxides from the knowledge that "early" first row transition metals oxides (situated on the left side of the periodic table) are more likely to initiate reduction reactions and "late" first row transition metals oxides (situated on the right side of the periodic table) are more likely to initiate oxidation reactions. Thus, established periodic trends suggest that oxidation tendency of these catalysts increases from left to right across the periodic table, from scandium oxide (reductive) to zinc oxide (oxidative). As a result, detection of an alcohol or compound containing a multiple bond would typically be accomplished using a late metal oxide, because these compounds are more susceptible to oxidative reactions. Detection of molecules possessing functional groups in higher oxidation states such as aldehydes, ketones, or carboxylic acids would typically be accomplished using an early metal oxide, because these compounds are more susceptible to reductive reactions. Often, these reductive reactions involve the transfer of hydrogen atoms from water vapor in the gas stream to the molecule being detected.

For low temperature adsorption analysis conditions, the catalyst can be qualitatively selected for a particular target molecule by choosing a complementary material that is expected to form a strong interaction with the target species, based upon the target's charge distribution, molecular polarity, ability to form hydrogen bonds, electronegativities of component atoms, and other such properties that affect the energetics of molecular adsorption at a catalytic surface. For example, the presence of O—H or N—H bonds in a target molecule would suggest the selection of a metal oxide, nitride, or fluoride catalyst, thereby encouraging hydrogen bond interactions between the target and the catalyst. A highly polar target molecule, containing chemical bonds between elements with a large electronegativity difference, would be expected to interact more effectively with a catalyst containing highly polar bonds and a similarly large electronegativity difference. Similarly, when a large electronegativity difference between an atom or group on a target molecule and an atom or group on the catalyst, the stronger and more effective the target-catalyst interaction. When catalytic materials are selected using well-known chemical principles such as these, a better complementary match and a stronger overall interaction between the target and catalyst may be achieved, resulting in a larger adsorption/desorption signal attainable at lower temperatures.

Simple oxide materials, such as those in Table 1 however are not required, however, as hydrous oxides, hydrated oxides, hydroxides, and even hydride compounds of metals can be used as catalysts. Crystalline and powdered metals can also be used, including but not limited to, ruthenium, rhodium, palladium, silver, gold, platinum, iridium, rhenium, combinations thereof, and the like. Metals such as these are especially useful as catalysts when operating this invention in the low temperature mode, as discussed below. Note that mixtures of metals and metal oxides can also be used as catalysts.

The sensing or reactive element of the sensor of this invention operates in conjunction with a reference element, which is simply a passivated HTD component without a catalyst coating. Thus, the reference element, which is used to provide an ambient baseline, is identical to the sensing/reactive element, except it is uncoated. The sensor is activated by passing an electrical current through the HTD that heats both the sensing and the reference elements, and affords a supply of electrons to electrostatically anchor a target molecule to the surface of a catalyst. When the sensing element contacts a target molecule, that molecule adheres or is attracted closer to the catalyst surface for a finite period of time, through a combination of electrostatic interactions, van der Waals forces, and the like. Upon any type of reaction between the molecule and the surface, such as an oxidation, reduction, any type of acid-base reaction, any bond-making or bond-breaking reaction, or merely adsorption and desorption, thermal energy is produced or consumed as a result of the net negative or positive reaction enthalpy, respectively. It is not just the sensing element that contacts a target molecule, but the reference element as well. Therefore, the sensor in fact compares the interaction between a specific molecule and the catalyst coated HTD (the sensing element), to the interaction of the same molecule and the uncoated HTD (the reference element).

Regardless of whether heating or cooling occurs, the temperature change associated with the reaction manifests itself as a resistivity change in the HTD circuit, which is detected electronically. The present sensor device allows selective detection of a target molecule, regardless of whether the discrete reaction process associated with detection is exothermic or endothermic.

This invention also allows quantitative information related to target molecule concentration to be obtained, because there is a direct correlation between the concentration of target molecules reacting with the catalyst coated HTD and the amount of heat produced or absorbed in the process. The amount of exchanged heat is then measured by the resulting voltage change and the corresponding electrical resistance difference between sensing element and reference element in the sensor circuit (the offset measurement strategy) or by the changes in electrical power to the VRH required to keep the temperature of the VRH at the desired level (the null-balance measurement strategy).

Temperature Ranges of Sensor Operation

Common resistance-type sensors presently in use, e.g. those that utilize a metal oxide such as $SnO_2$, operate at high temperatures on the basis of detecting a catalytic oxidation of a target molecule. The present invention is not so limited. While highly energetic reactions such as oxidation or reduction are readily detectable using the sensor of the present invention when operated in a relatively high temperature range, this invention also provides for target species detection based on lower energy processes, such as adsorption and desorption. Therefore, the present sensor is capable of obtaining specific qualitative and quantitative information from target molecules or substances at temperatures substantially lower than the classic high temperature range required when detection is based on highly energetic reactions.

High temperature sensing using this invention typically occurs from around 220° C. (although some reactions occur at lower temperatures) up to around 425° C. These specific high temperature chemical reactions typically relate to oxidation, reduction, and other relatively energetic reactions. The low temperature range of sensing typically relates to nondestructive adsorption and desorption or other primarily physical interactions between the target molecule and the heated sensing element, which is governed by the range of steric and electronic properties of both the target molecule and the catalyst surface. Low temperature detection is often used in the variable temperature mode of operating the invention, where for instance a temperature vs. heat flow diagram unique to a particular target molecular-catalyst surface interaction over a given temperature range is obtained, and can be stored and used in electronic form.

The low temperature range of detection typically occurs up to about 245° C. In any case, it is not critical to this invention that a chemical reaction in the classic sense actually occur, in which the target molecule reacts to form other molecules upon its detection. It is simply required that there exist a disparity in heat transfer at the sensing HTD versus the reference HTD due to some physical or chemical interaction between the target molecule and the catalyst. This disparity results from either no reaction at the reference HTD (when it is not catalyst coated), or a different reaction at the reference HTD, when it is coated by a different catalyst than the sensing HTD. The temperature range at which such interactions are observed to occur is typically between about −196° C. and about 260° C. More typically, many of these interactions are observed when the temperature of the sensing element and the reference element are regulated between about −78° C. and about 232° C. Even more typically, these interactions are observed between about 0° C. and about 232° C. Most typically, these interactions are observed when the temperature of the sensing element and the reference element are controlled between about 25° C. and about 200° C.

The low temperature range of detector operation applies generally to any type of relatively low energy interaction between target substance and sensor of the present invention. In particular, this feature relates to the unique energetics associated with adsorption or desorption processes between a molecule and the catalyst coating applied to the HTD, as compared with the energetics associated with the same process between that molecule and the non-coated reference HTD.

The electrical current used to activate the sensor heats the sensor, and additionally can supply electrons to electrostatically anchor a target molecule to the surface of a catalyst coated HTD. When a molecule adsorbs to or desorbs from the catalyst surface through electrostatic interactions, van der Waals forces, hydrogen bonding, and the like, thermal energy is produced or consumed as a result of the net negative or positive reaction enthalpy, respectively. The reactivity properties of both target molecule and catalyst that dictate their interaction are a function of, among other things, the molecular structure and electronic distribution or band structure of molecule and catalyst, the nature of the reactive sites on molecule and catalyst, the energy and symmetry properties of the HOMO and LUMO of both materials, and the physical chemical properties of the molecule-catalyst interaction itself. Heat is evolved when a molecule is adsorbed onto a surface, and heat is consumed when that molecule desorbs from that surface. This heat transfer process phenomenon is detected by the sensor and affords both qualitative and quantitative information. Thus, qualitative data results from the presence of a signal through the unique combination of target molecule, catalyst, and temperature at which a single species is detectable, while quantitative data arise from determining the amount of heat flow which is proportional to molecular concentration and voltage change at a given temperature during a physical chemical interaction or reaction at the sensing element. Qualitative measurements typically involve determining a detector response in the presence of a standard concentration of target molecule.

Figure 17:
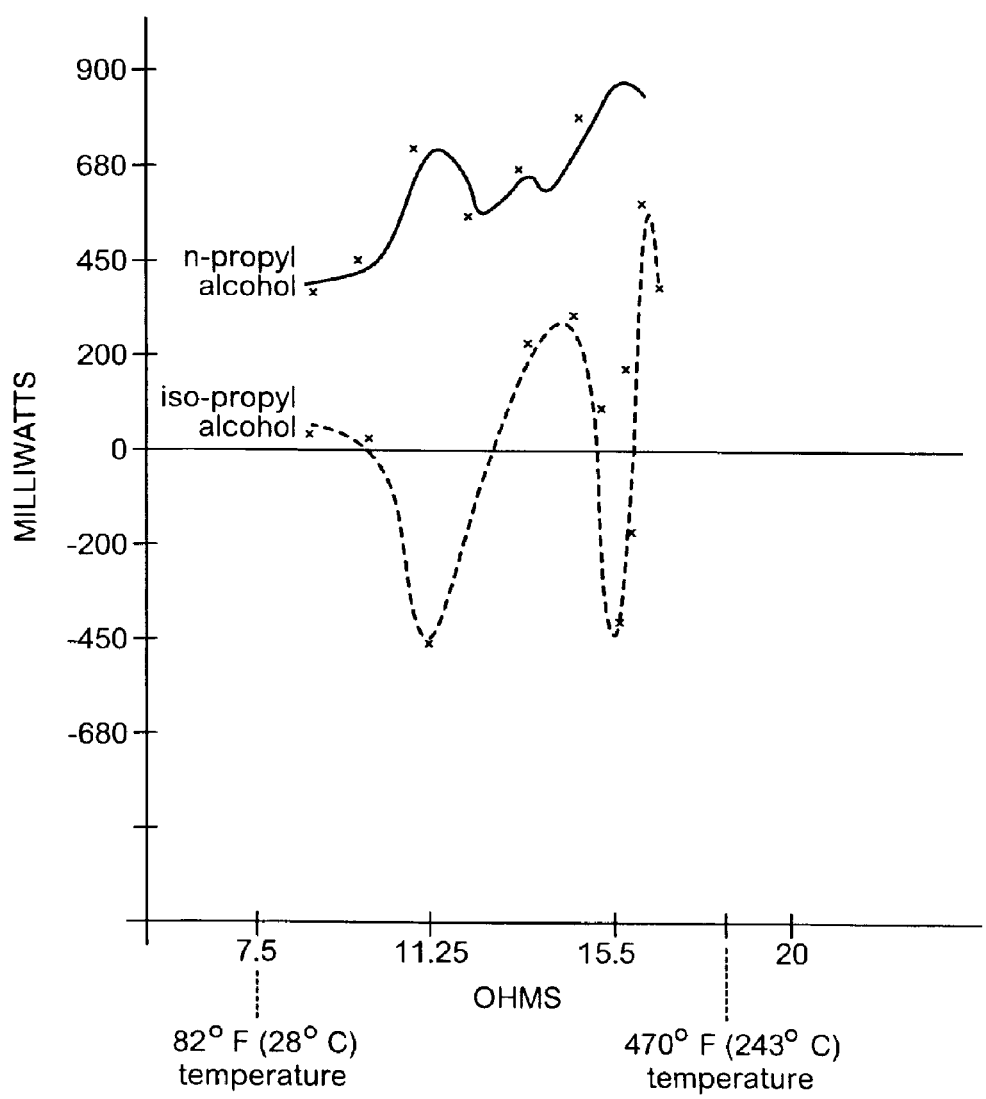
FIG. 17 is a low temperature detection plot of temperature (resistance) versus power for detecting 0.01% (vol/vol) isopropanol and 0.01% (vol/vol) n-propanol in air in the presence of a scandium oxide catalyst, at a sample gas flow rate of 2 mL/minute and an inlet gas temperature of 28° C.

While not intending to be bound by the following statement, it is believed that in the low temperature range, specificity arises by a different mechanism than in the high temperature reaction range of sensor operation. FIG. 17 presents a low temperature detection plot of temperature (resistance) versus power for detecting iso-propanol and n-propanol in air, demonstrating that the scandium oxide catalyst does not "ignore" one component over the other, but rather allows the generation of two distinctly different detection curves, thereby identifying both compounds simultaneously. Thus, low temperature specificity occurs with the ability to discriminate the two distinct chemical signatures at once. Identification of a particular component may require recording separate, standard response curves for each component of a mixture, to ensure accurate detection. In contrast, one may choose a catalyst that allows the selective adsorption of one component of a mixture, but not other components, thereby achieving specificity by formally "ignoring" the other species. In this latter case, specificity would be achieved in the same manner as in the high temperature range of detection.

Both low and high temperature ranges, as well as any intermediate temperature ranges for which some interaction between target molecule and sensor occurs, are useful in the present invention, regardless of whether the sensor is operated in the constant or variable temperature modes. Thus, a predetermined set of temperature/catalyst/target for a molecule may be used for detection of that target at low temperature. Further, a large range of temperatures, encompassing both low and high ranges, may be employed in the variable temperature (dynamic) mode as part of a programmed temperature vs. time profile, in which detector temperature is varied in a predetermined manner. In this aspect of this invention, a series of reactions of a particular target may be employed, from adsorption and desorption, to some acid-base reaction at the catalyst, to more energetic oxidation or reduction processes, in order to obtain very detailed qualitative and quantitative information on a target molecule. More importantly, when operated in a variable temperature (dynamic) mode, multiple target substances can be detected using a single HTD sensor, because different molecules interact with the catalyst coated sensor at different temperatures.

In another aspect of this invention, multiple sensors, coated with different catalysts, and all operated in a variable temperature fashion (but typically at substantially the same instantaneous temperature) are employed. When each sensor is operated with separate temperature control and monitoring electronics, calorimetric responses of each sensor are observed as temperature is cyclically and synchronously varied. Thus, multiple target molecules may be detected and measured simultaneously by collecting multi-dimensional data sets through a predetermined temperature cycling program.

Additional Means to Achieve Selectivity

Selectivity of the sensor device of this invention may be achieved through various adjustable parameters such as catalyst selection and sensor temperature. In addition, there are other means by which selectivity may be achieved, and thus by which different molecules that are structurally and electronically very similar may nonetheless be distinguished.

One further method to achieve selectivity, even when a single catalyst is employed, is by taking advantage of catalyst topology to discriminate between molecules. This concept involves varying the same catalyst's topology to achieve specificity, rather than varying catalyst identity. This catalyst topology mode of selectivity is effective under both high and low temperature conditions, involving both physical and/or chemical interactions. Thus, adjusting (depositing, exposing) which solid state face of a crystalline catalyst is exposed, in turn varies the energetics of molecular orientation at the crystal, which may permit more ready detection and discrimination between molecules, even when using a catalyst of the same molecular formula. A similar effect may arise by simply varying the solid state catalyst from one layer to multiple layers. It is possible that topology variations can give higher selectivities among target molecule-catalyst interactions than possible using simply catalyst identity to distinguish. For example using a noble metal, where a crystalline face might give a useless universal reaction to most molecules, whereas another crystalline face with a different atomic topology might allow specificity. Methods for depositing or exposing different crystalline faces are well established and known to one of ordinary skill in the art. Examples of selectively exposing one crystalline face of a catalyst are seen in the following references, which are incorporated herein by reference: D. F. Ogletree, M. A. Van Hove and G. A. Somorjai, *Surf. Sci.* 183, 1-20 (1987) for Pt(111) and M. I. Bán, M. A. Van Hove and G. A. Somorjai, *Surf. Sci.* 185, 355-72 (1987) for Pt(110); M. A. Van Hove and S. Y. Tong, *Surf. Sci.* 54, 91-100 (1976) for W(110) and W(100); C. Zhang, Van Hove and G. A. Somorjai, *Surf. Sci.* 149, 326-40 (1985) for Mo(100) and Mo(111); and J. P. Bibérian and M. A. Van Hove, *Surf. Sci.* 138, 361-89 (1984) for fcc(111) and hcp(0001) surfaces.

Another means to attain selectivity is by using an arrangement of HTD components in which a sensing element HTD has one type catalyst coating, and the "reference" element HTD has a different type catalyst coating, that is, the sensor is operated using two different sensing HTD elements. In this case, the invention typically uses a differential measurement between two sensing elements, which can provide a highly detailed information, including calorimetric spectroscopy curves, for analyzing target species. Further, differential measurements between two different sensing elements would provide valuable data when the first sensing element is coated with one crystalline face of a catalyst crystal, and the second sensing element is coated with a different crystalline face of the same catalyst crystal. In this case, common signal features resulting from identical interactions are subtracted out, and only energetic processes arising from the differences in interactions between the target species and a particular crystalline face are observed.

Yet another method to achieve selectivity is by varying the doping protocol of a semiconductor catalyst, which will afford discrimination among molecules, even with the same catalyst. In this "semiconductor catalyst mode" of selectivity, the catalyst constitutes, or acts as, a transistor, diode or other semiconductor. Specificity results from variations in the chemical and physical properties and the concentration of doped molecules that in turn affect the properties of the catalyst. Methods for doping semiconductors are well established and known to one of ordinary skill in the art.

Figure 1:
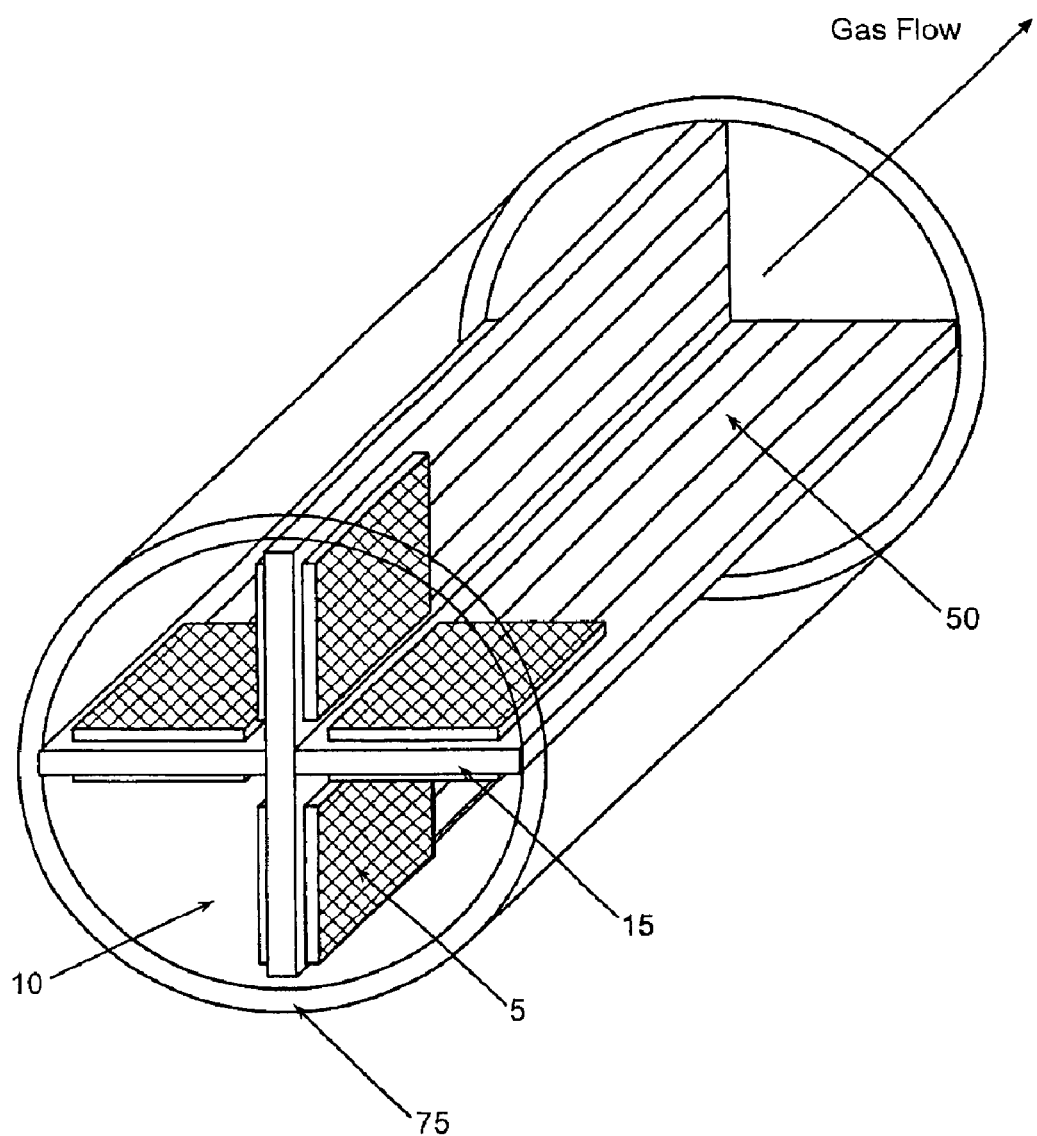
FIG. 1 illustrates one embodiment of a catalyst coated sensing HTD (FIG. 1A) and a non-coated reference HTD (FIG. 1B) of the present invention, both shown with electrical leads attached, and both immobilized on one side of a low thermal mass substrate.

Detailed Description of Various Embodiments of the Heat Transfer Device (HTD) Sensor Assembly FIG. 1 illustrates one embodiment of the heat transfer devices of this invention, demonstrating the structure of the catalyst coated sensing HTD 5 (FIG. 1A) and the reference HTD 10 (FIG. 1B). Sensing and reference HTDs are typically constructed on a supporting, low thermal capacity ceramic substrate 15, such as alumina, silica, titania, zirconia, other high melting point glasses, and the like. Both sensing and reference HTDs are made of an electrically resistive, VRH material 20 having a known temperature coefficient of resistance, typically in the form of a sputtered or printed layout pattern, that is immobilized on the support.

Sensing HTD 5 often includes a coating of high temperature resistant bonding agent or adhesive 25 (not visible in FIG. 1) on the electrically resistive VRH material 20, to which is bonded a layer of catalyst 30 so as to place the catalyst 30 in thermal contact with the VRH 20. In another embodiment, the catalyst coating 30 may be deposited onto the electrically resistive VRH material 20 directly, without the use of the high temperature adhesive 25. This latter embodiment is typical when a catalyst precursor metal is deposited on the supporting substrate electrochemically or by sputtering, followed by heating the HTD in air to convert the catalyst precursor metal into the corresponding metal oxide catalyst. The reference HTD 10 is typically passivated, most often with a temperature-resistant polymer coating or bonding agent 35 that prevents contact of the metal with the atmosphere. The high temperature resistant adhesive 25 used in the sensing HTD can be the same material as used in the temperature-resistant polymer coating or bonding agent 35, which makes the thermal resistance of the sensor and reference HTDs more nearly the same, but they are not required to be the same material.

The high conductivity circuit connection wires or metal tabs 40 are partially coated with copper or other high temperature solder-compatible conductor 45. Two electrical connection wires 50 are soldered to each connection tab 40 to enable use of the 4-wire (Kelvin) technique for electrical resistance measurement. Thus, both sensing 5 and reference 10 HTDs shown in FIG. 1 are connected to the signal conditioning electronics using the Kelvin circuit topology with four connecting wires 50 which, for convenience, exit the apparatus by a common wire covering 55 for connection with the signal conditioning apparatus. The four connecting wire, Kelvin circuit topology provides an electronic output which is essentially without uncertainties due to voltage drop or resistance change along the lead wire. For high temperature operation, lead wire attachment by spot welding may be preferred.

Both the ceramic or other high temperature supporting substrate and electrically resistive VRH materials are selected to operate without degradation at elevated temperatures. Examples of VRH materials that have a positive variable temperature coefficient of electrical resistance, include but are not limited to, transition metals such as nickel, tungsten, platinum, and the like. Varying amounts of chromium, cobalt, iron, and other common metals, may be included in the VRH material. In order for a VRH to have a single temperature associated with a particular electrical resistance, the VRH material must have substantially monotonically-variable temperature VRH of electrical resistance. This feature imparts a consistent slope to the resistance vs. temperature curve for the electrical conducting material, which neither flattens nor reverses. A reversal or change in algebraic sign in the slope would reflect that more than one temperature is associated with a particular electrical resistance. Particularly useful VRH materials have resistance vs. temperature curves characterized by a relatively large slope.

FIG. 2 illustrates two types of sensing HTDs 5. FIG. 2A represents a sensing HTD 5 with a layer of catalyst 30 situated directly on the surface of the sputtered or printed electrically resistive VRH material 20 without the use of a high temperature adhesive. In this example, the catalyst or catalyst precursor are typically electrochemically deposited or sputtered onto the surface of the VRH material 20. FIG. 2B represents a sensing HTD 5 with a coating of high temperature resistant bonding agent 25, to which is bonded a layer of catalyst 30, so as to place the catalyst in thermal contact with the VRH. In this example, the catalyst layer 30 may be either a "preformed" catalyst, such as metal oxide, or a catalyst precursor such as a metal that is later converted to a metal oxide catalyst or a noble metal with a specific crystalline face. The same arrangement of connection wires as illustrated in FIG. 1 is used in FIG. 2, thus, both types of sensing VRHs are connected to the signal conditioning electronics using the Kelvin circuit topology with four connecting wires 50 which, for convenience, exit the apparatus by a common wire covering 55 for connection with the amplification circuits.

FIG. 3 illustrates a generalized perspective view of one arrangement of the sensor assembly, illustrating the relative orientation of the major components including both sensing and reference HTD elements. The entire sensor assembly rests on a physical support 60, the principal utility of which is physical support, and thus requires sufficient rigidity. A thermal barrier 65 separates the sensing HTD 5 from the reference HTD 10. The thermal barrier functions to minimize radiation heat transfer between the sensor and reference HTDs. Spacers 70 are bonded to the thermal barrier 65 and the respective substrates 15 of each HTD 5 and 10. Spacers 70 are designed to typically provide about 2-3 mm distance between the thermal barrier 65 and HTDs 5 and 10. The electronic signal processing components of this invention are not shown in this view.

The active HTD element 5 and reference HTD element 10 are located an appropriate distance from the thermal barrier 65 so as to have no heating interference effect from barrier 65, while being sufficiently close to barrier 65 so minimal thermal heat transfer interference occurs due to conduction, convection and radiation between HTD elements 5 and 10, a distance which is maintained by spacers 70. In the embodiment shown, the sensing 5 and reference 10 HTD elements are positioned away from the thermal barrier and the spacers, thereby allowing effective sensing when the gas flow occurs in any direction parallel to the plane of the thermal barrier.

The physical support 60 often consists of a supporting channel with parallel sides, into which the sensor assembly can attach, and through which the connecting wires 50 may run. The support channel 60 shape provides an efficient anchor for 5, 10 and 65, while providing support for wires 50 as they exit the transducer tube in which the sensor assembly is contained. Support channel 60 is usually a relatively stiff metal such as copper consisting of a bottom and two parallel sides, though many other embodiments are possible. Support 60 provides support to the sensor assembly and allows it to be located as needed along the length of the support 60, and provides exit placement to allow the wires to exit the transducer tube that contains the sensor assembly.

Figure 4:
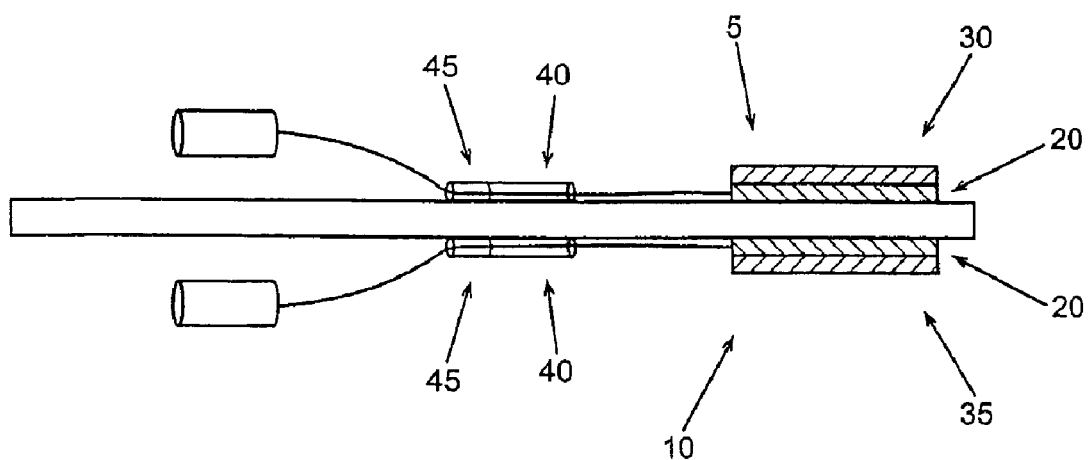
FIG. 4 represents a cross sectional drawings of one embodiment of the sensor assembly of this invention, in which the catalyst coated sensing HTD and the non-coated reference HTD are situated on opposite sides of the same low thermal mass supporting substrate.

An additional aspect and embodiment of the HTD sensing device is shown in FIG. 4, namely a combination or double-sided sensor-reference HTD in which sensing 5 and reference 10 elements situated on opposite sides of a single support. FIG. 4 illustrates the sensing HTD 5 with a layer of catalyst 30 situated directly on the surface (without coating of high temperature resistant adhesive 25), on one side of the thermally resistant supporting substrate. The reference HTD 10, passivated with a temperature-resistant polymer coating or bonding agent 35 that prevents contact of the reference HTD with the atmosphere, is positioned on the opposite side of substrate. The same arrangement of metal tabs 40, partially coated with high temperature solder-compatible conductor 45 that connects two wires 50 to each connection tab 40.

Figure 5:
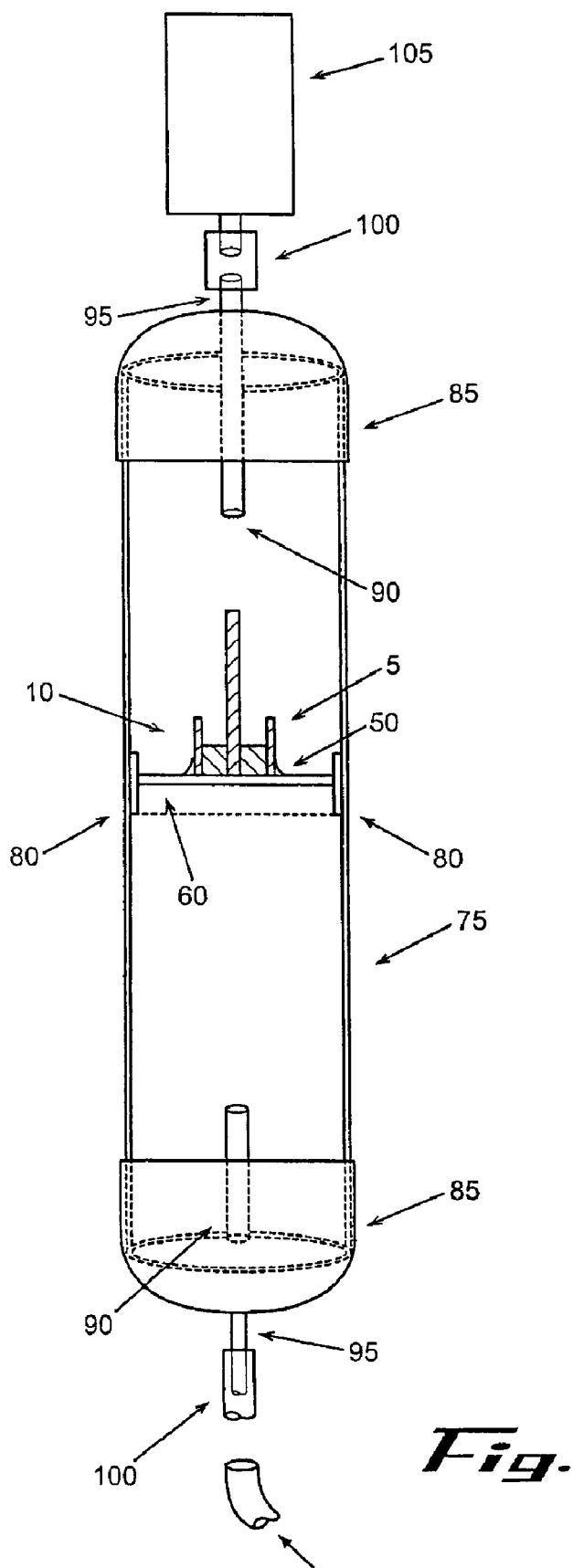
FIG. 5 illustrates one embodiment of a complete sensor of this invention in which air flow can be monitored and controlled by positioning the complete HTD sensor assembly in the interior of a high temperature-resistant transducer tube, through which a flow of gas is produced by a vacuum pump, and the opposite end of the tube is connected to a flexible hose that may be used to collect a sample of gas containing the molecule of interest.

Referring now to FIG. 5, the placement of the HTD assembly from FIG. 3 within the transducer tube 75 is shown. Transducer tube 75 functions to anchor the HTD assembly in such a manner that fluid (typically air) containing the target molecules of interest will flow parallel to the plane defined by the sensor assembly; thereby allowing the molecules to come in contact with the sensing 5 and reference 10 elements under substantially identical flow conditions and rates, and therefore permit sensing 5 and reference 10 elements to encounter the same concentration of target molecule. Wires 50 that maintain electrical contact to the sensor typically pass through the cylinder where the support 60 is secured to the interior walls of the transducer tube 75 via anchors 80. In the usual embodiment, gas tight end caps 85, with holes 90 centered in each cap, are placed over the ends of the cylindrical transducer tube 75. Typically, a short rigid tube 95 passes through holes 90 centered in each cap 85, and are secured in an airtight manner. The downstream end of a flexible hose 100 that attaches to the end of rigid tube 95 and attaches to small AC or DC vacuum pump 105 that pulls a gas stream over the HTD sensor assembly.

Figure 6:
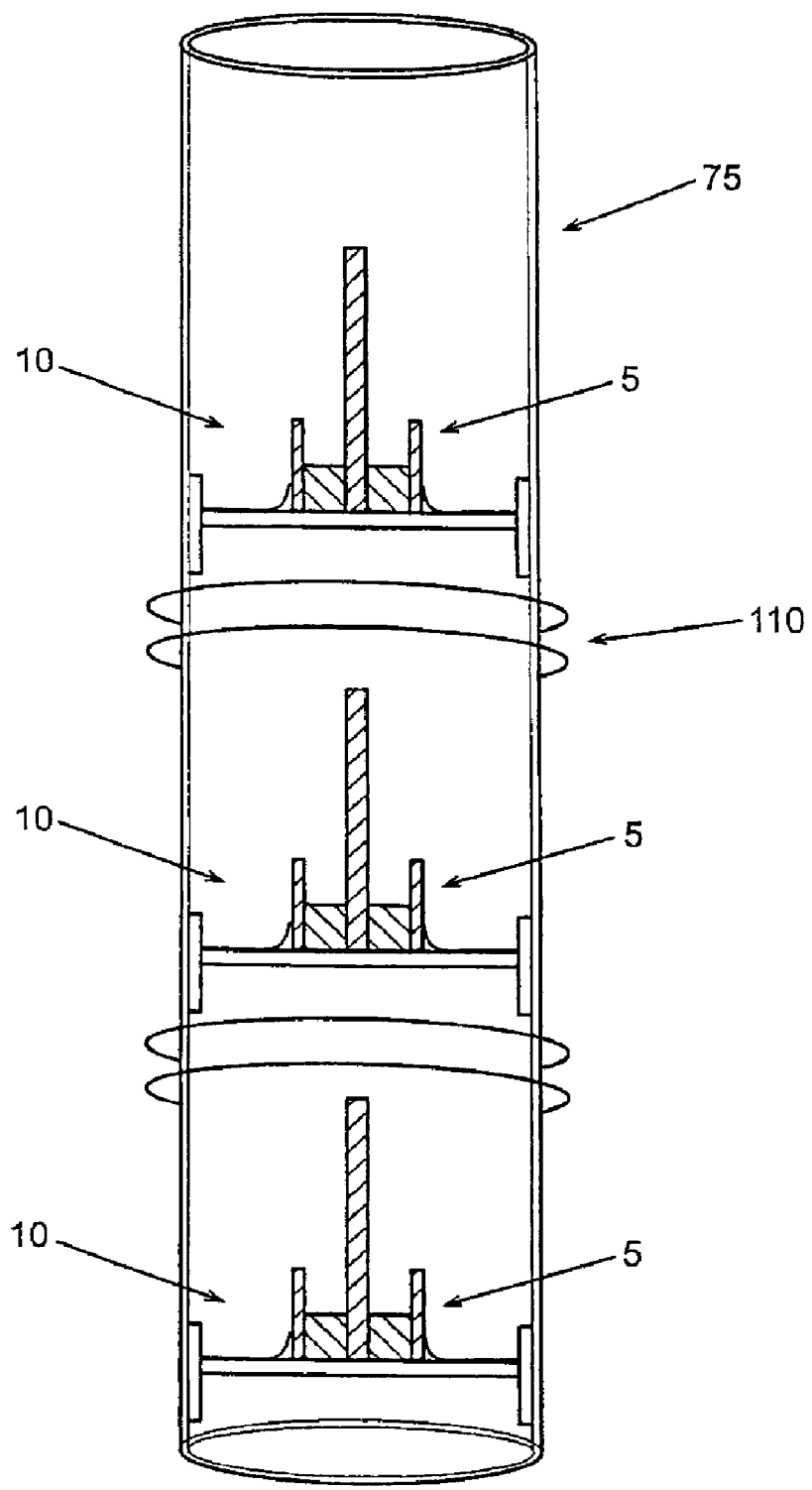
FIG. 6 illustrates one embodiment of a sensor of this invention in which multiple HTD sensor assemblies are situated in series within a single temperature-resistant transducer tube, thereby allowing the simultaneous detection and measurement of multiple gas phase molecules of interest.

The present invention allows multiple HTD sensors, often with different coatings, to be placed either in series or in parallel within the same flow transducer to detect additional molecules that have different types and classes of functional groups and/or different reaction temperatures. FIG. 6 illustrates one aspect of a sensor assembly containing multiple HTD sensor/reference assemblies in series. Such a configuration would allow for multiple target molecules to be analyzed at the same time with a single gas flow sample. While not always necessary, in a typical configuration the HTD assemblies would be placed far enough apart so that cooling of the sample would naturally occur as gas flow proceeds between the different HTD sensor/reference assemblies. For example, cooling could be enhanced by the use of cooling coils or cooling vanes 110 placed on the outer surface of the air flow transducer 75. The spacing of the sensor assemblies would be more of an issue with low temperature sensing when a gas stream requires cooling, rather than high temperature sensing where the gas stream is heated. Cooling becomes a potential issue if the sample gas arrives at the detector above the preferred detection temperature, in which case the gas sample must be pre-cooled upstream of the detector or the detector itself must be cooled to maintain the appropriate detector temperature.

Another embodiment of a multiple detector assembly is shown in FIG. 7, which depicts a parallel, or radial arrangement of seven sensor elements and one reference element. Radial arrangements such as FIG. 7 with more than this number of sensing elements are also envisioned. While multiple sensor HTDs are typically operated at substantially the same instantaneous temperature, if they are not, then a reference HTD will be useful at each different temperature and the physical arrangement of HTDs should take into account the fact that some HTDs are at a different temperature from other HTDs. One advantage of the parallel arrangement of HTDs in FIG. 7 as compared to a serial arrangement of FIG. 6 is that, because target molecules are detected in parallel, the composition of the gas stream being analyzed is identical at each sensor. Further, no cooling coils would typically be required in such an arrangement.

The sensor configuration of FIG. 7 is useful to situate a sensing and reference element on opposite sides of a single support, or two sensors on opposite sides of a single support, with the reference element located on a different support. Heat flow between sensor and reference VRH elements is undesirable because it minimizes the temperature difference that can develop between sensor and reference elements. However, there is essentially no opportunity for heat transfer between various VRH elements that are operated at substantially the same temperature. The configuration of FIG. 7 further anticipates a single reference element for a sensor assembly of any number of sensing elements, as well as more than one reference element for an assembly of sensing elements. An effective number of reference elements is that number that places at least one reference element in contact with substantially the same fluid stream which is being analyzed as any single sensing element.

A further aspect of this invention is the optional preheating or precooling of the fluid stream being analyzed, prior to its contact with the HTD sensor assembly. Precooling of the gas stream can increase the temperature range available for thermal spectroscopy and/or increase the thermal margin to a more useful level and minimize the likelihood or thermal saturation. In one embodiment, the sensor-transducer assembly can incorporate a heating element, such as a heating coil, upstream of the sensor assembly, to effect this preheating function. During operation of sensor, the reaction temperature at which the sensor operates is that temperature necessary to induce the discrete interaction on which detection is based, for a particular catalyst and target species. Therefore, preheating the gas stream is not a necessary step in detecting all target molecules. The heat required for the catalyst-molecule complex to surmount the activation barrier for reaction can be supplied by heating the catalyst (by heating the HTD), by heating the molecule (by preheating the gas stream), or both. Under normal operating conditions, the heated HTD transfers sufficient heat to the catalytic surface of the sensing element to raise its temperature to that specific temperature needed to cause the molecule in question to react. If insufficient heat is supplied to the HTD, a preheating element or coil can then be used to supply heat to the gas stream, and hence the target molecules being analyzed, such that the necessary interaction or reaction temperature is reached. Because preheating reduces the thermal margin of the detector, it may be beneficial in a situation where minimizing the electrical power required to heat the HTD is desired.

Figure 8:
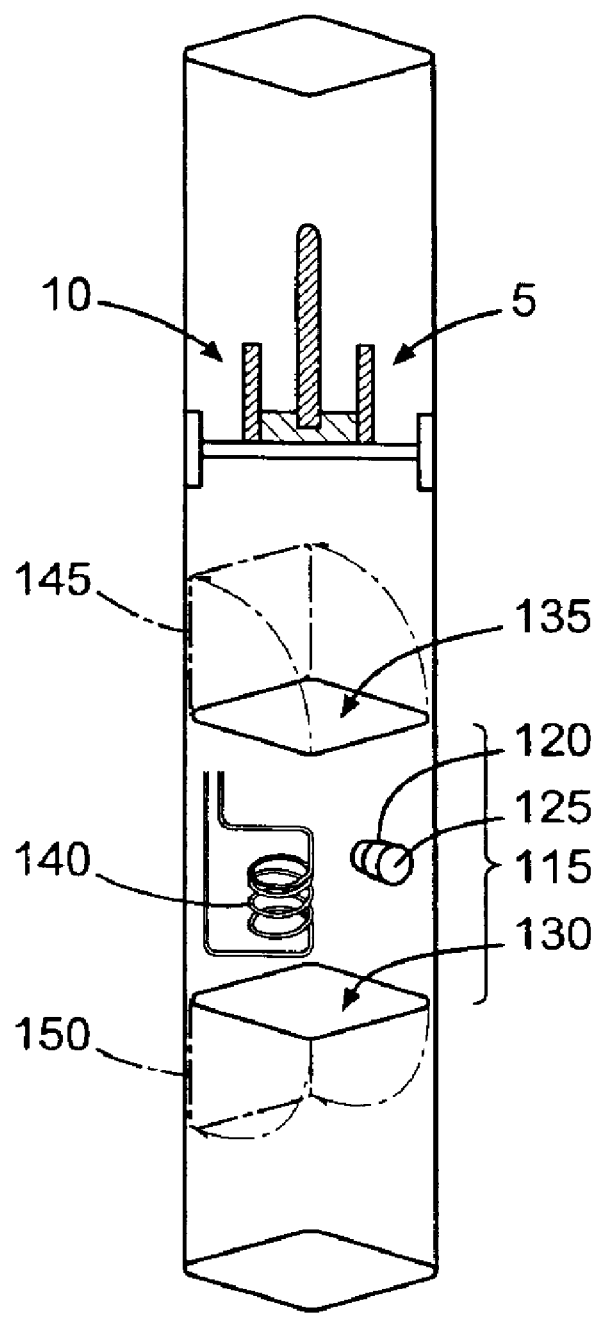
FIG. 8 illustrates an embodiment of the present invention in which a portion of the HTD sensor assembly and transducer tube are shown and are adapted for use with liquids that can be vaporized.

Another aspect of this invention, presented in FIG. 8, illustrates one configuration by which the transducer arrangement could be used for the analysis of molecules in a liquid. Chamber 115 is an airtight compartment, into which could be introduced a sample of liquid containing the target molecule of interest, through port 120. Port 120 is sealed with stopper 125 and isolated from the remainder of the transducer tube by bulkheads 130 and 135. Bulkheads 130 and 135 can be opened for access to the transducer tube at the appropriate time. During initial operation, with bulkheads 130 and 135 in their closed and airtight position, a sample of liquid would be placed in chamber 115 through port 120 and sealed with stopper 125. Heater coil 140 would vaporize the liquid, an airflow would be pumped through the tube while the moveable bulkheads would open to positions 145 and 150. Opening the bulkheads and inducing air flow would allow the heated vapor to flow through the cylinder and be sampled by the sensor assembly in the usual manner.

This invention is applicable to any substance that can be induced to form a gas phase molecule or material, whether that substance is a gas under ambient conditions, a liquid that can be vaporized, or a solid that can be sublimed. Therefore, a further aspect of this invention is the analysis of liquids or solids with this invention, in which the liquid or solid are brought into the gas phase by any means that is remote to the transducer arrangement as shown in FIG. 5. For example, a sampling device that is capable of collecting a quantity of a liquid or solid, and heating it sufficiently to volatilize it, can be used in conjunction with the HTD sensor assembly shown in FIG. 5 to sample and analyze liquid or solid materials.

As appreciated by one of ordinary skill, the aspects presented in these figures do not exclude additional or modified aspects in which the HTD sensor may be configured and utilized in a manner that could be adapted to suit a particular analysis at hand.

Examples of Additional HTD Sensor Element and Reference Element Designs

Figure 9:
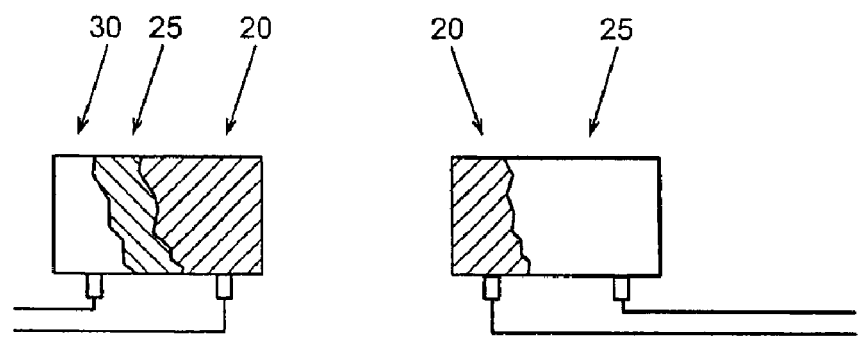
FIG. 9 represents a cut-away view of another embodiment of an HTD sensing element (FIG. 9A), in which the sensing element constitutes a rectangular solid of a resistance temperature detector (RTD) coated with a high temperature adhesive which adheres the catalyst coating to the substrate. An HTD reference element (FIG. 9B), in which a high temperature adhesive or bonding agent serves to passivate the layer, would be constructed similarly, but without the catalyst layer.

The HTD sensor assembly of this invention may assume different shapes and arrangements from that described above, as illustrated in FIG. 9. For example, referring to the HTD sensor (FIG. 9A) and reference (FIG. 9B) representations, an additional embodiment of the HTD sensing device is a solid sensing element with a rectangular, square or cylindrical or other shape which minimally inhibits air flow and allows high surface area to enhance the fluid sample-catalyst contact. Regardless of the shape, the ceramic or glass sensor and its positive resistive temperature VRH material 20 will be coated with a thin layer high temperature adhesive 25 which is further coated with a thin layer of powdered or granulated catalyst(s) 30, typically a metal oxide or other compounds or metals (FIG. 9A). The reference element (FIG. 9B) is essentially identical to the sensing HTD, but without the catalyst coating 30. Thus, in the embodiment shown in FIG. 9B, the reference element is passivated with the same thin layer high temperature adhesive 25 as used in the sensing element.

Figure 10:
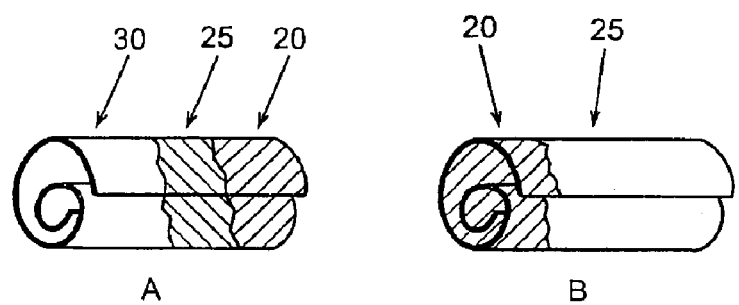
FIG. 10 represents a cut-away view of another embodiment of an HTD sensing element (FIG. 10A), in which the polyimide-encased sensing element constitutes a foil type, positive resistive temperature RTD sensing element, rolled to provide a high surface area sensing device, coated with a high temperature adhesive which adheres the catalyst coating to the substrate. An RTD reference element (FIG. 10B), in which a high temperature adhesive or bonding agent serves to passivate the layer, would be constructed similarly, but without the catalyst layer.

FIG. 10 represents another aspect of HTD sensor-reference assembly, utilizing rolled, foil type sensing elements. This type of HTD is designed to increase surface area and improve airflow properties around the sensor elements, and may have improved thermodynamic characteristics relative to the HTD sensor of FIG. 9. The foil sensor contains a positive resistive temperature HTD material 20 and is similarly coated with a thin layer of high temperature adhesive 25 which is further coated with a thin layer of metal oxide(s) or other catalyst(s) 30, then loosely rolled while retaining air-flow space between both surfaces of the foil along the entire length of the roll (FIG. 10A). The foil reference element (FIG. 10B) is essentially identical to the sensing HTD, but without the catalyst coating 30. In the embodiment shown in FIG. 10B, the foil reference element is passivated with the same thin layer high temperature adhesive 25 as used in the sensing element.

Figure 11A:
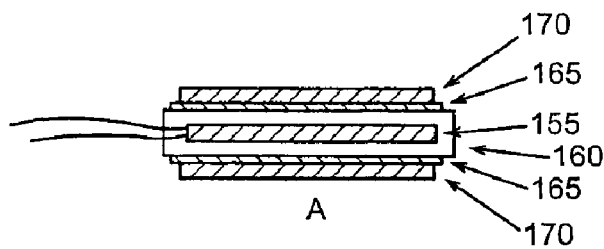
FIG. 11 represents a cross-sectional view of one embodiment of the catalyst coated sensing HTD (FIG. 11A) and the reference HTD with no catalyst coating (FIG. 11B) of the present invention, in which a metal foil was bonded to the sensing element VRH, and was subsequently oxidized to afford a metal oxide catalyst surface.
Figure 11B:
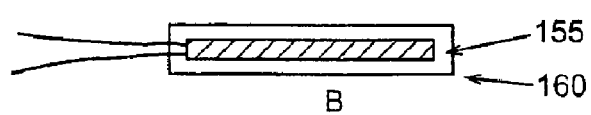

Another aspect of this invention applies to any of the catalyst-coated sensing HTDs illustrated or described here, namely an additional embodiment of the sensing HTD that involves a catalyst precursor attached to the HTD sensing element, rather than a preformed catalyst. For example, the HTD can be coated with a thin layer of pure metal foil such as copper, typically using a high temperature adhesive. The metal foil can subsequently be oxidized after adhesive curing by thermal or chemical means to afford a metal oxide catalyst surface, in this example, copper oxide. A cross-section of one embodiment of an HTD sensor of this type is shown in FIG. 11. In this embodiment, a platinum resistance heater element 155 is situated in the center of the HTD. A polyimide carrier 160, which provides an oxygen barrier between the gas stream and the HTD and supports the extremely thin foil, surrounds resistance element 155 such that together, 155 and 160 constitute the VRH portion of the sensor which serves as a non-catalytic heating function (VRH) and temperature detector function (RTD). This portion is common between sensing (FIG. 11A) and reference (FIG. 11B) element. High temperature adhesive 165 bonds metal foil 170 to the HTD body, which upon heating forms metal oxide layer on its exterior surface which serves as catalyst. FIG. 1B further illustrates the HTD reference element, which contains the resistance heater element 155 and the polyimide carrier 160 without the adhesive or metal foil.

An additional, very simple example of HTD sensing and reference elements of this invention is the use of a heated wire as the sensing HTD, while the same type heated wire that is passivated constitutes the reference HTD. A sensor and reference of this type combine all three functions of the variable resistance heater (VRH), resistance temperature detector (RTD), and catalyst in a single metal wire (for example, gold). Thus, the reference wire is required to be passivated to prevent its reaction.

Theoretical Considerations of Molecular Detection

While not intending to be bound by the following theory, it is believed that the high selectivity of the sensor device of the present invention arises as follows. As electrical current passes through the VRH, it resistively heats and excites the chemical bonds within the catalyst coating. Typically, these bonds are metal-oxygen bonds, in which case the reaction associated with detection of the target molecule is likely to be an oxidation or reduction. Higher temperatures of the sensing element induce a greater excitation energy of the catalyst metal-oxygen bonds, until the point at which an energetic match occurs between the metal-oxygen bond energy and the oxidation or reduction potential of a target molecule. Reaction ensues at this match point, in this case by transfer of an oxygen atom from a broken metal oxide bond to the target molecule, and a heat of reaction is detected. A quantum electron tunneling phenomenon at the energetic match point may contribute to the selectivity of this sensor and method. Reduction can also occur when matched energy allows various reactions with hydrogen atoms from gas phase water or other sources, including from other molecules or sources within the gas stream.

While not intending to be bound by the following statement, it is also believed that the reactivity properties in general of both target molecule and catalyst are a function of, among other things, the molecular and electronic structure of the target molecule, the solid state and band structure of the catalyst, the nature of the reactive site, the energy and symmetry properties of the HOMO and LUMO of both materials, as well as the energy, symmetry, and electrostatic properties of the molecule-catalyst interaction itself. A signal represented by the catalyst being further heated by the bond energy of oxidation or reduction of the target molecule being detected as a reaction-induced temperature variation. By varying the sensors' VRH current, the temperature of the catalyst will vary and the sensor(s) will discriminate molecules and/or concentrations. Thus, there appears to be a unique combination of molecular properties of the target molecule (including symmetry, electrostatic, and energetic considerations), properties of the catalyst, (symmetry, electrostatic, and energetic properties, temperature, composition, etc.), VRH current that provides heat to the catalyst, and so forth, that results in a discrete reaction of a single molecular species. This result is believed to arise from the differential between the bond energies of the metal oxygen bond (or other bond types) of the sensor coating and oxidation or reduction potential of the target molecule's active site, as well as variability of the temperature of the sensor, physical interactions such as adsorption, and the like. Therefore, the current of the sensor VRH can be varied to initiate the reaction or a unique adsorption/desorption profile of a given molecule, and only a molecule that is capable of interacting with, and is being supplied with, this unique energy will react, or produce that unique adsorption/desorption profile. Other molecules with different structural and electronic properties will not react nor affect the temperature change at the sensor, and therefore the signal temperature is unique to any combination of target molecule, catalyst, and given current.

These same theoretic considerations could also be operable in the present invention regardless of the type of reaction that the target molecule undergoes, as both exothermic and endothermic reactions can be detected. For example, the exothermic reaction energy for most oxidations results in a positive temperature change in the metal oxide coating, whereas endothermic reactions would induce a negative temperature change. In either case, the temperature change manifests itself as an electrical resistance change in the VRH circuit that is electronically detected. In the case of an oxidation, it is likely that an atmospheric $O_2$ molecule splits allowing one atom to replace the oxygen site on the vacated metal, thus regenerating the original metallic oxide. The other oxygen atom would react with the target molecule, e.g. displace two hydrogen atoms to form water, or to simply transfer to the target molecule forming higher oxidation state species. Reductive reactions would likely be characterized by analogous reactions involving electron and/or hydrogen transfer with atmospheric water as their probable source. Adsorption and desorption reactions would also manifest selectivity as either endothermic or exothermic processes. While not intending to be bound by the following statement, it is also believed that the release or "out-gassing" of electrons from the activated sensor electrostatically may attract or anchor the target molecule to the metal oxide or other catalytic surface. Signal specificity is achieved by an interaction between a current in the VRH's resistive core heating the external catalyst to such a degree that there is an interaction with a chemical bond of the target molecule in a manner that creates an oxidation, a reduction, or a unique adsorption/desorption profile.

Electronics Component for Detecting Target Molecules and Substances in the Constant Temperature Mode of Operation The variable-resistance heater (VRH) of the present invention is typically formed on a low thermal mass and capacity substrate from which heat flow to the environment is minimized. Typically, the catalyst coated sensor VRH and the non-coated reference VRH are each connected to signal conditioning electronics with four connecting wires using the Kelvin measurement circuit topology. While the commonly used Wheatstone bridge topology with two or three lead wires to a VRH will function in this application, the Kelvin topology substantially eliminates the attenuation and contamination of signals common in bridge topology implementations due to lead wire impedance effects. To more fully understand the signal conditioning electronics used to operate the sensor assembly of this invention, thermodynamic models of sensor operation presented in terms of an electronic paradigm are provided in Example 17.

The typical measurement means is to use the method of constant-temperature calorimetry to signal condition the variable-resistance sensor assembly. Micko (U.S. Pat. No. 4,305,724) and Young (U.S. Pat. Nos. 5,989,398 and 6,071,476) describe complex pulsed analog and direct digital control aspects of constant temperature calorimetry, respectively, both of which are incorporated herein by reference. The present invention encompasses an improved implementation of the constant-temperature calorimetric method in a continuous analog feature that requires fewer components, provides more information, and improves on performance. By connecting both sensing and reference VRH elements through the Anderson Loop circuitry as described in U.S. Pat. No. 5,371,469 (incorporated herein by reference) and using the differential measurement mode, the output voltage signal requires no further data processing to remove the primary systematic errors from the data.

Figure 12:
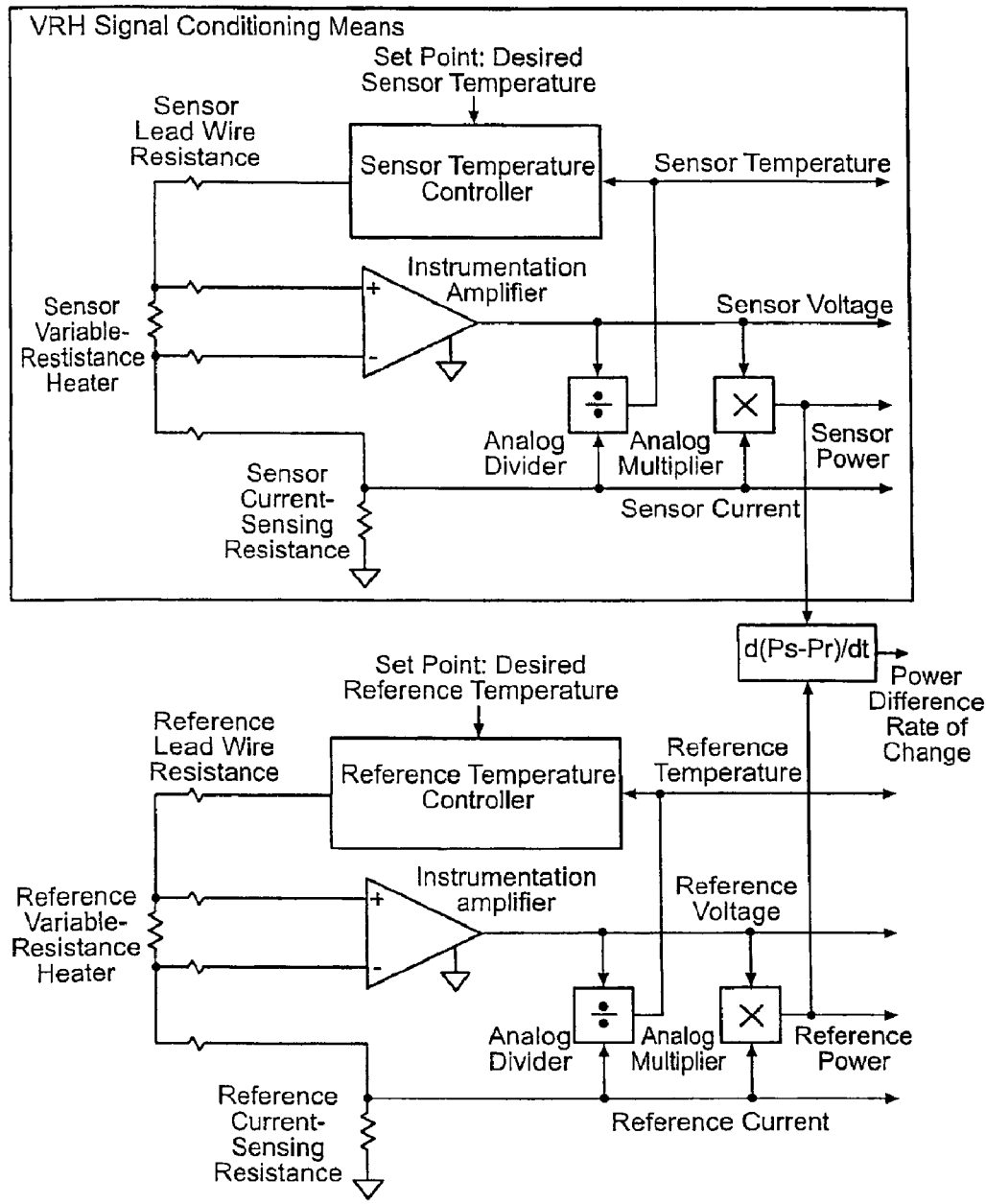
FIG. 12 represents a schematic diagram of one embodiment of the conditioning electronics of the present invention, specifically for the null-balance measurement strategy.

FIG. 12 illustrates a block diagram of one embodiment of the signal conditioning means for a null-balance measurement strategy, in which the amount of heat in terms of electrical power required to hold the HTD at substantially the desired instantaneous temperature is measured as an indication of thermal activity. The portion of FIG. 12 that is enclosed in a block represents the signal conditioning associated with each sensor HTD in a detector. Thus, the detector assembly of FIG. 7 having seven sensor HTDs and one reference HTD would require signal conditioning consisting of seven sets of the apparatus enclosed in the block of FIG. 12, each set conditioning one of the seven sensor HTDs working with one set of the substantially identical apparatus connected to the single reference HTD in FIG. 7.

Figure 13:
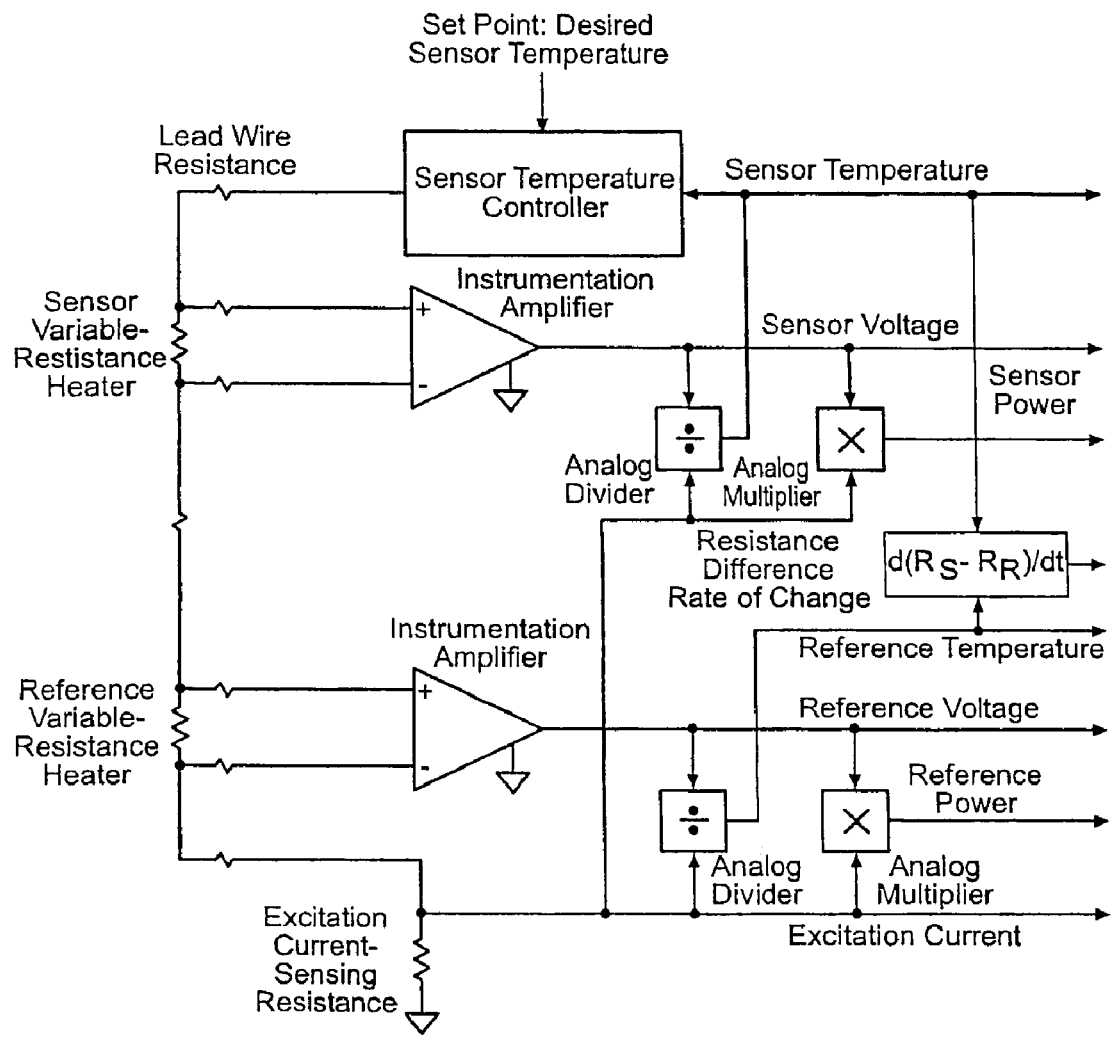
FIG. 13 represents a schematic diagram of one embodiment of the conditioning electronics of the present invention, specifically for the offset measurement strategy.

FIG. 13 illustrates a block diagram of one embodiment of the signal conditioning means for an offset measurement strategy, in which the active sensor's change in temperature due to catalytic activity with respect to the temperature of the reference HTD is observed as a measure of thermal activity. The offset measurement strategy usually requires a substantial thermal resistance between a sensor HTD and its associated reference HTD so that a temperature difference (offset) can develop between them. Thus the HTD configurations depicted in FIGS. 4 and 7, having lower thermal resistance between sensor and reference HTDs as compared to those depicted in FIGS. 3, 5, 6, and 8, typically performs less well with the signal conditioning arrangement of FIG. 13.

A single temperature-variable electrical resistance in each of the sensing and reference elements serves simultaneously as heater and temperature sensor. FIG. 12 present a schematic design of one embodiment of the continuous analog constant-temperature calorimeter electronics of the present invention. Two high-speed analog multiplier-divider components (Analog Devices AD538) develop output voltages representing the ratio of the voltage across, and the current through, the sensing and reference elements. These analog output voltages are representative of the electrical resistance (R=E/I) and thereby the temperature of the variable-resistance sensing and reference heater elements. As shown in FIG. 12, these analog signals are used as feedback for comparison in a set point potential in a fast analog control loop. The set point potential commands the control electronics to cause the variable-resistance heater to substantially achieve a desired operating temperature. The electrical set point potential can be provided by either a manual adjustment or by a computer through a digital-to-analog converter and can be varied with time for calorimetric spectroscopy.

One aspect of this invention uses a computer which receives high-resolution measurements of the voltage across, and the current through, the sensing and reference variable-resistance heating elements. Computer software is employed to subsequently estimate the transfer functions of the sensor and reference temperature HTDs and their respective temperature controllers, and operate to adjust their respective set point potentials to minimize the difference between the desired and the measured heater temperatures to typically within 0.1 to 0.2° C. As catalytically-generated heat is added to or subtracted from the active sensing element as described above, the electrical power required to maintain the element at its desired operating temperature is lowered or raised respectively in order to maintain the sensing element at substantially the desired temperature.

In the embodiment shown in FIG. 12, the analog signals whose ratios represent the heating element resistances are also provided as the multiplied inputs to two additional analog multiplier-divider components. The analog multiplier outputs are continuous representations of the electrical power required to maintain the sensing and reference heater elements at substantially the same temperature. The electrical potential difference between the multiplier outputs represents the difference in electrical power applied to the sensing and reference heating elements, and thereby indicates the magnitude and direction of heat flow resulting from catalytic reactions at the sensing element. In this aspect, the power difference signal is mathematically differentiated using a standard electronic differentiator circuit whose output then represents the rate of change of the catalytically-generated heat flow to the active sensor. This output provides a substantially immediate notification of any change in the concentration of the specific molecule the active sensor is observing.

Because concentration and rate of change of concentration data are continuously available from the sensor, this invention is readily adapted for use in applications where continuous monitoring of contaminants is desired, such as analyzing transient gas concentrations. Further, this sensor is suitable for sample analysis where it is desired to locate the sensor itself and the electronic component a significant distance from each other. This capability allows the device to be used where a probe must be located directly in a fluid stream, or combined with other electronic devices under feedback control, such as in automobile emissions systems.

High-resolution measurements of the sensing and reference element voltage drop and current used to calculate sensor and reference resistance (R=E/I) as described above can also be used to digitally calculate the difference in electrical power applied to the sensing and reference elements (P=E·I) and the rate of change of the difference in the active and reference variable-resistance heating elements (dP=dE·dI). The digital approach becomes the typical approach when a digital controller is available and the time delays inherent in sequential digital systems can be tolerated. To minimize measurement inconsistencies that could lead to errors in resistance and power calculations, it is typical that the same reference voltage is used for generating all set point control signals and as the reference input to the analog-to-digital converters used for all digital estimates of voltage drop across, and current through, the sensing VRH and reference VRH elements.

Accordingly, the unique interaction (whether an oxidation, a reduction, an adsorption, a desorption, an acid-base reaction, a hydrogen-bonding process, a van der Waals interaction, an electrostatic interaction, a bond-making reaction, a bond-breaking reaction, or a combination thereof) between a target molecule and the catalyst coated HTD surface, with respect to the uncoated (or differently-coated) reference HTD, provides an electronic signal in volts, power, or other convenient units. The voltage necessary to desorb a given molecule from a specific surface at a given temperature is also unique, and a temperature vs. voltage profile with respect to the reference will uniquely identify the molecule and its concentration.

Thus, it can be seen that the present invention differs from previous sensors in many ways, including but not limited to the following. The present invention does not purposely cause combustion of the target molecule, since low temperature as well as high temperature modes of detection are possible, and because any type of energetic interaction between the target molecule and catalyst coating can be used for detection purposes. The present invention further uses a continuous, independent temperature control system rather than switching methods which produce unwanted noise in the process of regulating the sensor and reference temperatures. Thus, a smooth, rapid temperature control is accomplished without the use of bridge circuitry and its inherent reduction in measurement sensitivity. Several sensor elements may be deployed simultaneously in a detector of the present invention, sharing a single reference element. The use of low voltage circuitry allows for battery operation of the sensor, and the present invention provides the ability to detect molecules using either exothermic or endothermic reactions, affording tremendous versatility. Typically, this invention continuously calculates power changes with respect to a reference for readout, rather than averaging the area of a control pulse. Additionally, temperature sweeps can be relatively rapid with this invention, and stabilization with gas concentration changes is rapid.

Electronics Component for Detecting Target Molecules and Substances in the Calorimetric Spectroscopy Mode of Operation The previous section detailed how the sensing and reference elements are connected to signal conditioning electronics using the Kelvin circuit topology, for constant temperature operation, for detecting a single target substance at each sensor. This section details how detecting multiple target species at a single sensor is achieved by operating the detector in a variable temperature, calorimetric spectroscopy mode. This variable temperature mode of detection involves varying the sensor temperature over time in a cyclic manner, and continuously monitoring the calorimetric response over the entire range of temperature variation. This process yields data in which specific molecules are characterized by predetermined patterns of calorimetric response vs. temperature that can be analyzed by readily available pattern recognition software. Thus, for a specific catalyst coating, a particular substance will be detected by some predetermined pattern of response over some predetermined temperature range, while a different substance will be detected at the same catalyst by some other predetermined pattern of response appearing in some other predetermined temperature range. The exact catalyst coating employed, and the range of temperatures traversed, dictate what target species may be measured with that specific sensor. Note that while calorimetric response vs. temperature patterns are most often determined by experimentation, a qualitative understanding of the target molecule-catalyst interaction can be gained by knowledge of the target molecule's functional groups and electrostatic characteristics, as well as the catalyst's chemical properties based such features as the location in the periodic table of the metal that forms the oxide catalyst.

The calorimetric spectroscopy (variable temperature) mode involves a programmed temperature vs. time profile, in which detector temperature, specifically both sensing and reference elements, is varied in a predetermined manner. When the sensor assembly is operated in the calorimetric spectroscopy mode, multiple target substances can be detected using a single HTD sensor, because different molecules interact with the catalyst coated sensor to provide different response patterns at different temperatures.

A very useful feature of the calorimetric spectroscopy mode of this invention is capable of gathering multi-dimensional data sets utilizing multiple sensors, each typically coated with a different catalyst, and all operated in a variable temperature fashion, though usually (but not necessarily) at substantially the same instantaneous temperature. When each sensing and reference element is operated with separate and substantially identical temperature control and monitoring electronics, correlatable calorimetric responses from each sensor are observed as temperature is cyclically and synchronously varied. In this manner, multiple target molecules may be detected and measured simultaneously by collecting multi-dimensional data sets through a predetermined temperature cycling program. One embodiment of a multiple sensor array that is well adapted to the calorimetric spectroscopy mode is that shown in FIG. 7, which depicts a parallel, or radial arrangement of seven sensor elements and one reference element.

The detectors of FIGS. 4 and 7 are typically operated using the null-balance measurement strategy in which the instantaneous temperature of the sensor VRH and reference VRH are controlled to be substantially identical. There is theoretically no heat flow between two VRH elements at the same temperature so each VRH temperature controller is essentially unaffected by heat transfer from the other VRH. It is preferable that sample gas flow be the primary means for cooling the sensing and reference VRH elements, because the rate of heat flow that occurs away from the surface Of these heat transfer devices, through conduction, radiation, and convection, determines the rapidity at which temperature cycling can occur. Further, incorporating a relatively high temperature limit in the temperature cycling profile provides for clearing the catalyst of any residual adsorbed material that might interfere with further measurement.

Standard multi-dimensional correlation techniques routinely used in various disciplines for pattern recognition and image processing can be adapted to refer to predetermined and electronically stored response patterns. These reference patterns can be used to compare and recognize experimentally obtained data from the calorimetric response and thereby identify specific molecules. This method achieves the virtually simultaneous identification of the presence and concentration of multiple target molecules in near real time. Electronics for this manner of operation are programmed to accomplish data gathering, in combination with standard pattern recognition software such as found in or adapted from standard spectometric analysis instrumentation such as mass spectrometry, nuclear magnetic resonance, and Fourier-transform infrared instruments.

The multi-dimensional, multi-sensor detector described herein consists of apparatus and methods for detecting observed energy flow (for example in Joules per second, or Watts), occurring at each sensor simultaneously. Thermal spectroscopy is achieved by establishing detector temperature variations in a cyclic manner by means of closed loop control systems and recording, displaying and analyzing estimates of detector electrical power dissipation associated with various temperatures within the spectrum of temperature variations established by the multiple electrical VRH resistance control systems. Obviously, temperature variations can extend over a wide range, a narrow range, or even held to substantially zero as may be useful for any set of specific target molecules to be detected.

The ability of the control system to smoothly regulate VRH electrical resistance establishes the fundamental resolution of the detector output, which can be especially important in multidimensional detection. The smooth regulation of VRH electrical resistance depends directly upon the capability to estimate VRH electrical resistance from voltage and current measurements. Analog division means, for example the Analog Devices AD538, inherently operate with signals observed at substantially the same instant and is capable of achieving a resolution of one part in 10,000. While digital-to-analog conversions can achieve far greater resolutions, the results of multiplications and divisions from digital estimates of analog levels are inherently delayed from the time at which the estimates were made, and typically exhibit resulting resolutions that are poorer than those achieved by direct analog processing. The performance of the overall measurement system is thus fundamentally limited by the performance of the detector, which can be analyzed with a thermal model appropriate for the mechanical design under consideration, as described in detail in Example 17.

Figure 14:
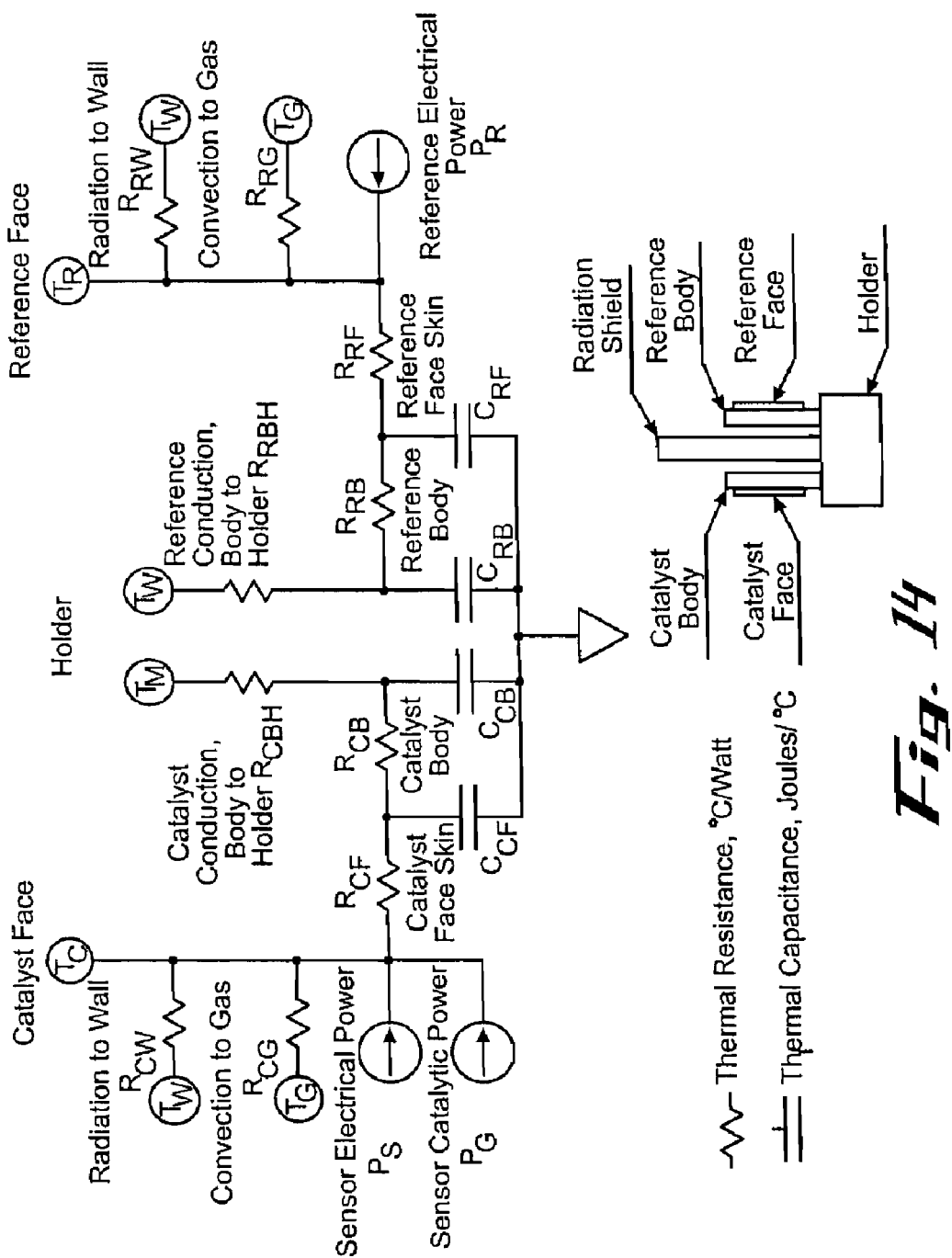
FIG. 14 illustrates one thermodynamic model of sensor assembly and operation in terms of an electronic paradigm, in which the catalyst-coated sensing VRH and the reference VRH are situated on separate bodies.
Figure 15:
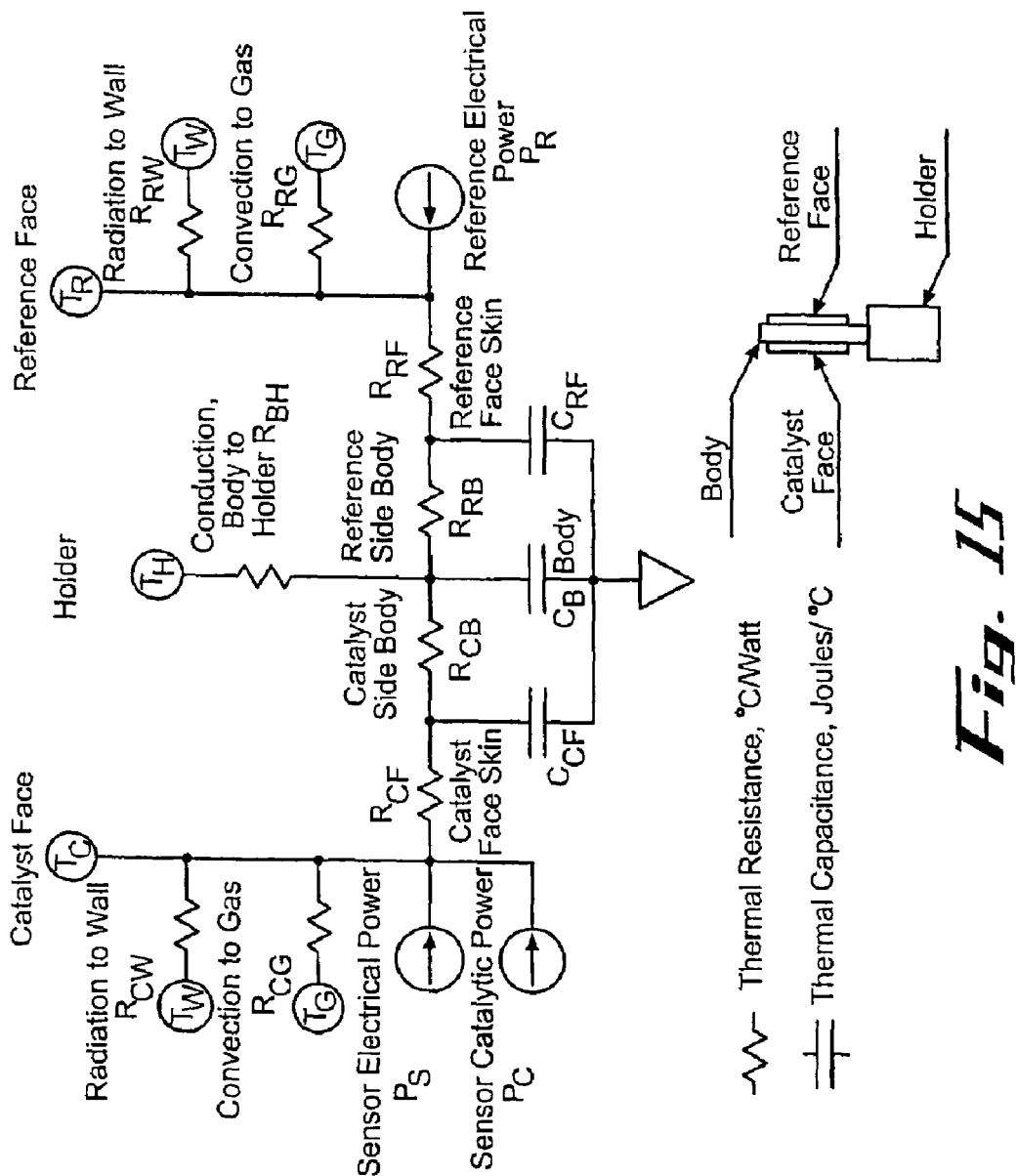
FIG. 15 illustrates one thermodynamic model of sensor assembly and operation in terms of an electronic paradigm, in which the catalyst-coated sensing VRH and the reference VRH are situated on the same ceramic body.

Thermal Models of Sensor Operation in the Calorimetric Spectroscopy Mode as an Electronic Paradigm FIGS. 14 and 15 present thermodynamic models of two different aspects of the present invention. These thermodynamic models are useful for all measurement and operational modes and can provide useful predictions of the performance and limitations of the modeled configurations. FIG. 14 illustrates one thermodynamic model of sensor assembly and operation in terms of an electronic paradigm, in which the catalyst-coated sensing VRH and the reference VRH are situated on separate bodies, as in FIG. 3. FIG. 15 illustrates one thermodynamic model of sensor assembly and operation in terms of an electronic paradigm for analysis and calculation convenience, in which the catalyst-coated sensing VRH and the reference VRH are situated on the same ceramic body, as in FIG. 4. In either case, both sensor and reference VRH elements are generally heated electrically to achieve substantially the same instantaneous temperature. An electronic control system establishes the appropriate HTD temperature which is typically varied cyclically as a function of time, though in some measurement methods the HTD temperature may be held constant. Because the heater has an electrical resistance that varies monotonically with temperature, typically (but not necessarily) with a positive temperature coefficient of resistance, the instantaneous temperature of the heater can be estimated by observing the electrical resistance of the HTD. Temperature control is effected by means of controlling the electrical resistance of the HTD through its dissipation of electrical power arriving from the sensor or reference electrical power source, modeled as current sources.

As the schematics of FIGS. 14 and 15 indicate, in estimating temperature levels and time histories in this variable temperature analysis, the proxy for thermal energy is electrical charge, while the proxy for temperature is electrical potential. Thermal resistance and thermal capacity are modeled as electrical resistance and electrical capacity, respectively. Similarly, the thermodynamics of temperature variations are modeled by the time histories of electrical current flow and the resulting potentials. Thus, the HTD elements exchange electrical energy for substantially the same amount of thermal energy (for example, both measured in Joules), at a measured rate (for example, Joules/second or Watts), indicated by the sensor and reference electrical power sources. Because both endothermic and exothermic processes are encompassed by this invention, this energy conversion is operable in both directions. The energy dissipated in the HTD raises the temperature of the outer surface of the catalyst and to a small depth beneath the catalyst, or "face skin" region, that the target molecule contacts exponentially to the temperature at which the rate of thermal energy arriving at the face is balanced by the rate at which thermal energy leaving the face through the network of thermal resistances (which represent temperature drop caused by heat energy flow rate in ° C./Watt). Time constants describing the observed exponential temperature variations are likewise modeled by the thermal resistances and capacities, defined as temperature change per unit of stored thermal energy in ° C./Joule.

The presence of catalytic material on the HTD sensing element provides for the transfer of thermal energy, either exothermic or endothermic, due to various modes of catalytic activity, as compared to the HTD reference element. Independent electronic control systems vary the electrical power applied to the HTD sensing or reference elements such that their electrical resistances result in substantially the same instantaneous temperatures as a function of time. Energy (Joules), whether delivered by catalytic or electrical energy sources, has substantially the same thermal effect, therefore catalytically-developed energy can be analyzed as substituting interchangeably for electrically developed energy. The rate of delivery (arrival or departure) of catalytically-developed energy can be estimated by the difference between the level of electrical power required to maintain the desired electrical resistances of the sensor and reference HTD elements.

Thermal saturation occurs when the desired HTD electrical resistance is attained without the need to dissipate electrical power. Thus, thermal saturation results at a given ambient condition when the rate of heat energy arriving from catalytic activity is equal to or greater than the electrical power required to maintain the desired HTD electrical resistance without catalytic activity. The susceptibility of a sensor to thermal saturation depends on the various ambient temperatures to which the sensor transfers heat energy and the ability of the sensor to deliver heat energy to its surroundings. An important feature of these thermal models is that they can be used to estimate the rate of catalytic activity that results in thermal saturation at the sensing element.

Thermal saturation does not typically limit measurement range when using the offset measurement strategy. However, if the sensor HTD increases in temperature due to catalytic activity, the higher catalyst temperature may not remain optimum for observing the target molecule. This effect is termed thermal detuning.

The thermomechanical structure of the sensing element is designed by choosing materials, physical dimensions, mounting for the sensing element, and flow conditions that will permit heat energy to depart by conduction, convection and radiation at a rate that will keep the HTD at a temperature substantially lower than the intended HTD operational temperature. For example, separating the sensor HTD from its holder by longer, lower cross-sectional area material with a higher insulation value will increase thermal resistance. A sensor body composed of material having a lower thermal capacity reduces HTD thermal capacities. Greater heat transfer to the gas flow lowers thermal resistance as does radiation to a lower-temperature environment. If the interior of the passage in which HTDs are mounted is polished metal, silvered, gold plated, or the like, then radiation heat transfer will be minimized and the thermal resistance due to radiation will increase. As a practical matter, a detector is built first and its performance is subsequently determined. The design of the detector is then adjusted to achieve greater utility by adjusting physical arrangements to achieve more appropriate thermal resistances and capacities. Clearly, the more sensitive a sensing element is to small levels of catalytic activity the more susceptible the sensor will be to thermal saturation.

Another feature of the FIGS. 14 and 15 models is the ability to estimate the impact of a change in temperature of the sensor on the resistance of the HTD of its associated reference element. The crosstalk interactions between sensing and reference HTD control systems are driven by this effect. By design, operation of the sensing and reference HTD elements at substantially identical instantaneous temperatures results in minimal thermal energy flow from the sensor to the reference even when the detector temperature is varying under the control of a thermal spectrometer.

Further Applications of the HTD Sensor Device and Methods

In addition to the applications and methods of using this sensor device described above, there are many other applications for, and methods of using this invention. The following examples are representative of the many potential applications of the sensor and methods of this invention, and are not to be considered exhaustive. For any target species, qualitative and quantitative analysis of that species are carried out in the usual way for any analytical technique, using unique resistance (proportional to temperature) versus power plots or current versus voltage plots as shown in the Examples, to uniquely identify a target species, and/or determining a response for a concentration standard to gain quantitative information.

Examples of potential applications for this invention include the rapid, non-invasive measurement and determination of medical conditions. For example, the concentration and ratio of acetone to methyl ethyl ketone can be determined from which glucose levels can be calculated. The presence of specific nitrogenous metabolites can be determined and related to the presence and concentration of opiates in the blood stream. Clearly, tests for blood alcohol levels, drugs, or drug byproducts in the breath or perspiration of motorists, truck drivers, bus drivers, train engineers, ship or barge captains, pilots, heavy equipment operators, athletes, or medical patients may be obtained by the direct measurement of the offending species or its breakdown products. Rapid assessment of battlefield injuries is possible, as is the direct measurement of anesthetic concentrations during surgery. Monitoring patients for a range of medical conditions is possible before, during, and after surgery using this invention, which is especially useful for unconscious or uncooperative patients. A range of diseases and conditions are detectable using this invention, because any molecule, species, pathogen, and the like—whether a drug, drug byproduct, metabolite, indicator for a condition or disease, or a condition precursor—that can be induced to form a gas phase material can be detected. This capability makes this invention useful in the diagnosis of cancer, heart disease, renal function, liver function, and countless other internal medical conditions.

The security and anti-terrorism applications of this invention are similarly broad. Explosives and explosive residues are detectable by, among other things, continuous gas phase sampling to screen passengers, airline crews, ground crews, airport workers of all types, luggage, air freight, and containers of all types. Security checkpoints, jetways, waiting rooms, airplanes, baggage holding areas, baggage cars, food service vehicles, fuel and maintenance vehicles, and the like, can be fitted with small devices of this type, for detection purposes. Similarly, devices can be located anywhere detection is a concern, including the ground level proximate to an aircraft. In many situations, molecular concentration measurements using multiple sensors simultaneously could used to triangulate and locate the source of a target substance, in any application. It is important to note that biological weapons and hazards, as well as chemical ones, may be detected with this invention, thereby making is particularly useful in the fight against terrorism. Thus, anthrax, smallpox, other mono- or multicellular organisms or viruses, and the like can all be detected with this method, because of the unique energetics of associating these species with the surface of a particular catalyst, at a particular temperature. The portability of these devices makes them well-suited for monitoring toxins at sites where potential terrorist attacks or harmful chemical spills or seepage might have occurred. This invention may even find use for continuous monitoring of characteristic gases of geologic origin, for volcano and earthquake prediction data.

The mobility of this sensor device renders it applicable to deployment in automobiles, piloted or non-piloted planes, boats, and the like. Further, detectors can be miniaturized to provide small, handheld devices for detection purposes. This feature could permit sensor use under any field condition, for example in sensing operations for EPA compliance using mobile or remote sensors, for drug detection by the DEA, or for atmospheric testing by NOAA. Sensor operation itself could readily be automated, and data from the sensor could be transmitted to remote data monitoring stations for analysis. Further, military and police units could use such a device to determine the presence of contraband materials, explosives, chemical or biological agents, and the like. The ability to sense molecules in boxcars, container ships, and the like before unloading their contents onto tractor trailer trucks for transportation, would greatly facilitate and enhance security measures. This sensor could be mounted in an unpiloted aircraft which, using Global Positioning Satellite (GPS) data, could engage in detecting illegal or dangerous substances by flying a predetermined flight pattern and providing concentration data correlated to location. In this instance, a map of concentration data would allow ready source location of the target substance.

Detection using these devices is sufficiently inexpensive and rapid that essentially 100% of the containers entering this country through ports, containers crossing borders by truck or rail, and every bag of every passenger entering the U.S. by any means can be tested. The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to one of ordinary skill in the art without departing from the spirit of the present invention or the scope of the appended claims.

EXAMPLE 1

Construction of a VRH Sensor Element Using a Powder Catalyst

A VRH sensor was prepared using a preformed, powder catalyst as follows. This sensor can be operated using either the offset or null-balance measurement strategy and in either the single channel (single-ended) mode or the dual channel (differential) mode. The VRH consisted of a single filament, 12 volt Sylvania #53 lamp. The filament was exposed by carefully cracking and removing the glass from the bulb assembly. Once exposed, the filament was coated on all sides with M Bond 600 strain gauge adhesive (Vishay Measurements Group, Raleigh, N.C.), freshly prepared according to product directions. Immediately after coating, the surface of the filament was covered completely with a 360 Mesh catalyst powder. Therefore, the M Bond adhesive serves the dual functions of passivating the filament and adhering the catalyst coating to the filament. All powdered catalysts tested in this manner were applied as 360 mesh size for consistency. When filament coating was complete, the filament assembly with attached electrical leads was placed in a preheated, 120° C. oven and cured for 3 hours. The oven was turned off and allowed to equilibrate to room temperature for about 30 minutes.

EXAMPLE 2

Construction of a VRH Sensor Element Using Electroplating to Produce a High Temperature Resistant Coating A VRH sensor element was prepared using an electrolytic solution to produce a high temperature resistant coating as follows. This sensor is most useful where adhesives for catalyst powders can not withstand high operating temperatures. The sensor described here can also be operated in either the single channel mode or the dual channel mode. A VRH consisting of a single filament, 12 volt Sylvania #53 lamp, was obtained as described in Example 1. Using a length of 24 gauge copper wire as an anode, a conduction wire from the coil was connected to a constant voltage source (Cole-Palmer Instrument Co. Insteck DC power supply, #PS-18300) via the ground connection. The copper wire was similarly connected to the constant voltage source at the positive voltage connection. Both the electrically connected filament coil and the copper wire were placed in contact with an aqueous solution of 0.01% copper sulfate. The voltage source was allowed to deliver 0.05 amps across the circuit for a period of 4 seconds, to electrolytically plate a layer of copper onto the filament. The copper-coated coil was removed from the solution, washed with water to remove excess copper sulfate, and air-dried. The coil was then brought to a temperature of 93° C. for 15 minutes by connecting it to the voltage source with a current of 3V and 0.03 amps, after which time it was allowed to cool. This heating step converted the copper coating to a copper oxide coating on the sensor VRH element.

EXAMPLE 3

Construction of a VRH Reference Element

A VRH reference element was prepared as follows. A VRH consisting of a single filament, 12 volt Sylvania #53 lamp, was obtained as described in Example 1. This filament was then passivated by applying a coating of M Bond 600 to the filament, then immediately coating the M Bond film with 360 mesh aluminum oxide (Alfa Aesar #42572). Its application is identical with the application of catalyst powder as described in Example 1. Aluminum oxide powder as applied with M Bond 600 is used to help the filament resist higher operating conditions. When filament coating was complete, this reference VRH with attached electrical leads was placed in a preheated, 120-125° C. oven and cured for 3 hours. The oven was turned off and allowed to equilibrate to room temperature for about 30 minutes.

EXAMPLE 4

Construction of a Sensor Assembly Using a Single Sensor HTD

Figure 16:
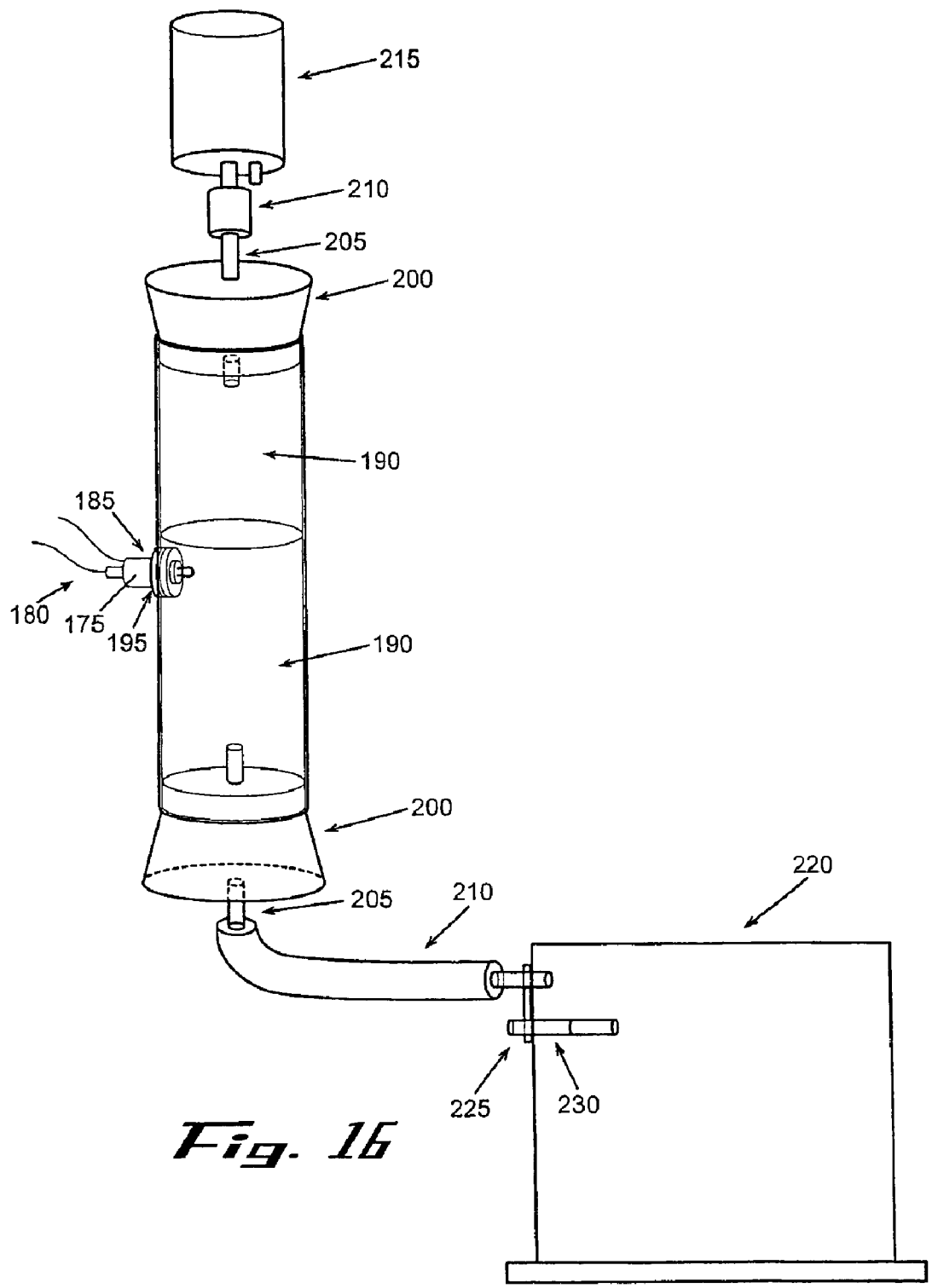
FIG. 16 illustrates a one embodiment of a sensing element of this invention, adapted for single-ended measurements (without continual use of a reference HTD). In this embodiment, the transducer tube contains either the HTD sensing element or the HTD reference element, but not both at the same time.

The construction of the embodiment of a sensing element of FIG. 16, adapted for single HTD rather than differential HTD measurements. As described in this Example, this embodiment has the transducer tube with the sensor HTD element or the reference HTD element only, rather than both sensor and reference at the same time. The cured sensor assembly 175 from Example 1 has two wires 180 soldered to the lamp's cylindrical metal holder for connection with the amplifier circuitry, at points on either side of the sensor circuitry. Further, the lamp's metal filament holder allows support for a "V"-shaped loop of heater filament. The metal holder is surrounded by a vinyl grommet 185 as shown in FIG. 16 for securing through a glass transducer tube.

A glass tube 190 (Pyrex #7740 tubing; Wale Co., Inc. #BS-022), with an interior diameter of about 23 mm and length of about 75 mm, has a notch 195 placed therein, of a size which will hold the lamp-grommet assembly in a firm manner, as illustrated in FIG. 16. Another identical glass tube 190 without a notch is placed on top of the tube-VRH sensor and is secured in place with a Masking Tape (for example, 3M, general purpose Masking Tape, #2050), not shown in FIG. 16. Further air leakage at the joiner of the glass tubes can be prevented by using a compound such as Super Glue's Handi-Tak (#5059596). Holes are bored in corks (Cole-Palmer #7754-18) 200, and a tube 205 (for example, K&S Engineering Round Brass #1148) is inserted through each hole as illustrated in FIG. 16 to allow air flow through the entire apparatus.

A length of polyvinyl chloride tube (Fisher Scientific Co. #14-176-217) 210 is placed over both metal gas tubes. One tube connects with vacuum pump 215 (ASF Thomas, G 6/04EB # 0108000776), while the other tube is connected to an air tight container 220 (US Plastics #65019). The capacity of sample container 220 is about 5 gallons or about 19 liters. Another tube 225 adapted for holding a thermometer is inserted through the wall of container 220, fitted with a thermometer 230, and made airtight. Pump 215 is activated using a low flow rate (as indicated by Cole Palmer's mass flow detector u-32600-02, gas from container 220 is drawn into the sensor tube as shown in FIG. 16 and across the sensor assembly 175, after which it is exhausted. Air flow during a detector run is low (around 1 mL/min) and the run takes a relatively short time, therefore little gas is removed from container 220. Typically, following a detection run, the seal between the thermometer 230 and its tube 225 is broken to allow atmospheric pressure equalization.

EXAMPLE 5

Low Temperature Operation of a Single Channel VRH Sensor to Detect Target Species The VRH sensor of the present invention is operated in the low temperature range to detect the presence of a target species, using the following protocol. This Example illustrates detector operation using the more simple, single VRH mode, in which data were collected over a range of temperatures first in air under identical conditions as those used to collect data for a target molecule. The background (baseline, non-reactive air) data were then subtracted from the target molecule data in order to substantially correct for systematic errors due to environmental variation. During operation of the sensor, the temperature of the coils was measured using an IR detector (Infrared Thermometer #U-39800-02, Cole-Palmer Instrument Co.).

A typical detection test using a sample liquid or gas added to sample container 220, is carried out as follows. A known amount of a liquid or gas sample, which has been calculated to achieve a known molecular concentration after vaporization of the liquid or complete mixing of the gas, is added to container 220 which has a known volume. In the case of a liquid, container 220 is shaken for about 30 seconds, then allowed to stand for about 1 hour to permit complete vaporization of the liquid. A heating pad can be used to gently heat the container to aid in vaporization of the liquid, and in regulating the sample gas to the desired temperature. Temperatures around 75-85° F. were commonly employed.

The signal conditioning electronics were turned on, the temperature of the gas was measured, the vacuum pump is activated, and a slow gas flow (around 1 mL/min) was initiated. The flow was monitored by Cole Palmer's mass flow meter U-32600-02. Gas flow continued for about 1 minute prior to starting detection, to ensure a constant target molecule concentration throughout the gas flow path. For single HTD operation, a detection scan was initially measured on an air sample from a 5 gallon container, without the target species, to establish a baseline. A second, identical detection scan is then taken on the sample from the 5 gallon container which was prepared with the target species of interest. After the target molecule and non-reactive air data were collected over a range of HTD temperatures, the air data were subtracted from the target molecule data to achieve the desired absolute molecular data. The above experiment was repeated in the offset mode using a differential measurement for confirmation.

EXAMPLE 6

Data Processing for Single Channel Operation of the VRH Sensor

Data interpretation relates power required to maintain sensor temperature to target molecule concentration, in the following way. Power (in watts, for example) is the instantaneous product of voltage and current across the sensor or reference. Power is also expressed as heat flow at the sensor, for example in Joules per second. Energy which is produced or consumed at the sensor by various physical and chemical processes manifests itself as heat being released or absorbed, for a given set of conditions such as temperature, catalyst, gas flow rate, and target molecule. The rate at which heat is produced or released is proportional to target molecule concentration, therefore power is proportional to molecular concentration.

The interaction between the target molecule and the catalyst coated sensor results in heat exchange arising from the interaction between molecule and catalyst. This heat exchange from this interaction tends to cause a change in sensor temperature. The electronic components of the sensor apparatus (FIGS. 12 and 13) are employed to maintain the sensing element at substantially the desired instantaneous temperature, which requires the addition (or dissipation) of a certain amount of power, depending upon molecular concentration. The power required for maintaining substantially the desired instantaneous temperature, which derives either from non-catalytic electrical "heat power" provided by the electronic circuitry of FIGS. 12 and 13, or "catalytic power" arising through some type of physical or chemical interaction between target molecule and catalyst. When the concentration of target molecules is relatively high, most or substantially all of the power arises from catalytic sources. If the molecular concentration is low, a greater proportion of the power required to maintain the temperature substantially where desired must be supplied by the electronic circuitry of this invention. As a result, the smaller the electrical power required to maintain sensor temperature, the greater the amount of catalytic power is available to maintain a given temperature, and therefore the higher the concentration of target molecules present in the sample gas. Conversely, the larger the electrical power required to maintain sensor temperature, the lower the amount of available catalytic power, and the lower the concentration of target molecules present in the gas sample.

As a result of this relationship between temperature, power, and molecular concentration, the power and temperature data are used as follows. A plot of sensor electrical resistance (which is proportional to temperature) on the X-axis, versus voltage or power (whether electrical or catalytic) on the Y axis results in a curve whose shape, position and magnitude along the X axis serve to uniquely identify a target molecule, as well as its concentration for a given set of conditions. The temperature range is noted on data provided in the Figures. Conditions that affect the shape and position of the curve include, but are not limited to, the particular catalyst used, the catalyst topology, the target molecule, the sensor temperature, and the like. Conditions that affect the magnitude of the curve variations include, but are not limited to, the concentration of the target molecule, and signal conditioning limitations such as thermal saturation and amplifier saturation, if present. Thus, more unique identifying curves can be obtained by using different catalysts, temperatures, topologies, as well as other conditions.

EXAMPLE 7

Low Temperature Operation of a VRH Sensor to Distinguish iso-Propanol from n-Propanol Using the protocol detailed in Examples 5 and 6, the sensor device may be used to identify and distinguish iso-propanol from n-propanol.

FIG. 17 is a plot of power versus temperature for 0.01% (vol/vol) iso-propanol and 0.01% (vol/vol) n-propanol in air, detected in the low temperature mode using a scandium oxide catalyst, coated on the sensing VRH. Sample gas flow rate was 2 mL/minute, at an inlet gas temperature of temperature of 28° C. The data for the two alcohols were taken separately in two different runs. These data illustrate how the unique power versus temperature curves for iso-propanol and n-propanol allow their unambiguous identification.

EXAMPLE 8

Low Temperature Operation of a VRH Sensor to Detect Nitrobenzene

Figure 18:
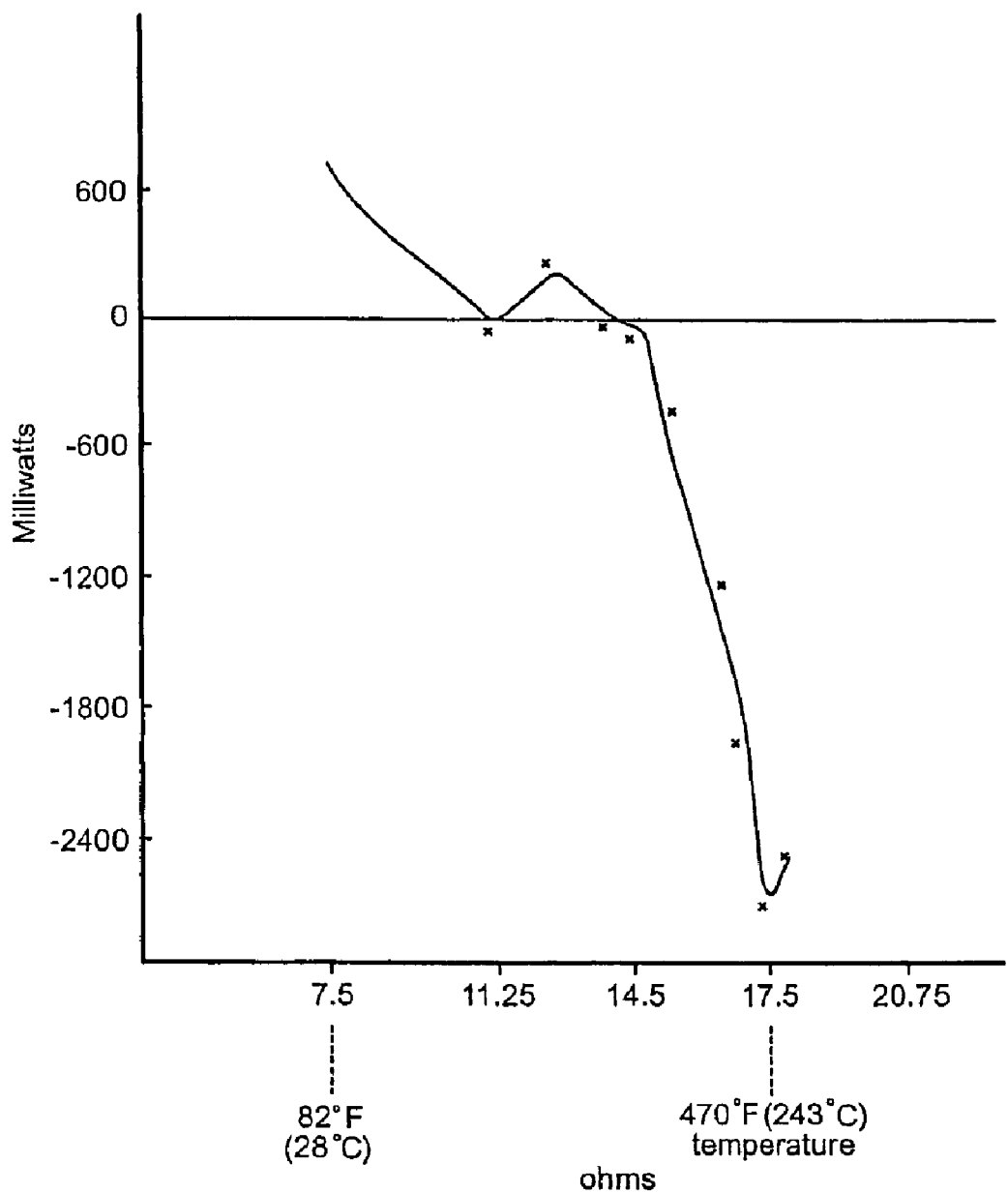
FIG. 18 is a low temperature detection plot of temperature (resistance) versus power for detecting 0.01% (vol/vol) nitrobenzene in air in the presence of a scandium oxide catalyst, at a sample gas flow rate of 2 mL/minute and an inlet gas temperature of 28° C.

Using the protocol detailed in Examples 5 and 6, the sensor device may be used to identify and measure nitro compounds such as nitrobenzene. FIG. 18 is a plot of power versus temperature for 0.01% (vol/vol) nitrobenzene in air, detected in the low temperature mode using a sensing VRH coated with a scandium oxide catalyst. Sample gas flow rate was 2 mL/minute, at an inlet gas temperature of temperature of 28° C. These data illustrate how the power versus temperature curve uniquely identifies nitrobenzene for a given set of conditions, and how readily this curve is distinguished from data for compounds such as iso-propanol and n-propanol, even under identical detection conditions.

EXAMPLE 9

Figure 19:
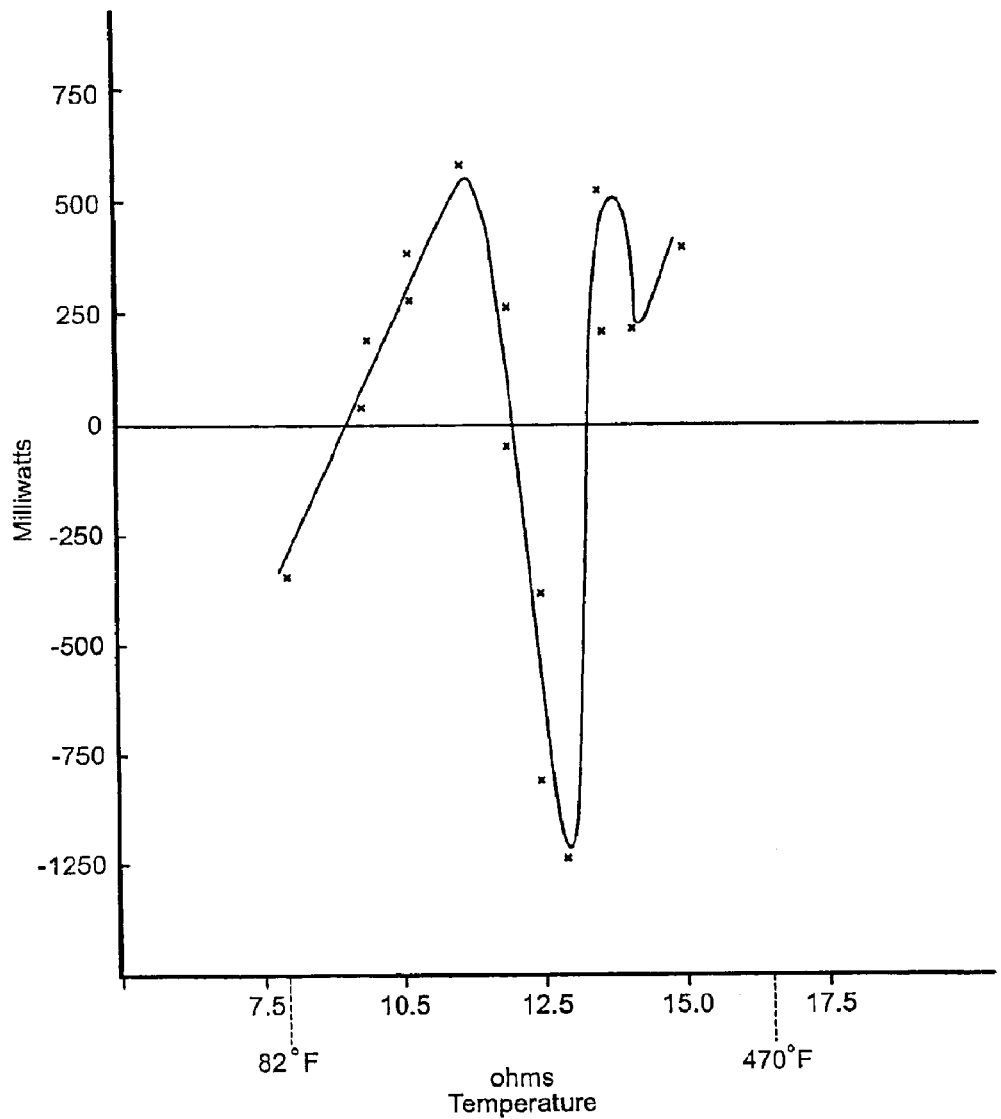
FIG. 19 is a low temperature detection plot of temperature (resistance) versus power for detecting 0.01% (vol/vol) ethanol in air in the presence of a scandium oxide catalyst, at a sample gas flow rate of 2 mL/minute and an inlet gas temperature of 28° C.

Low Temperature Operation of a VRH Sensor to Detect Ethanol at a Scandium Oxide Catalyst Using the protocol detailed in Examples 5 and 6, the sensor device may be used to identify and measure ethanol. FIG. 19 is a plot of power versus temperature for 0.01% (vol/vol) ethanol in air, detected in the low temperature mode using a sensing VRH coated with a scandium oxide catalyst. Sample gas flow rate was 2 mL/minute, at an inlet gas temperature of temperature of 28° C. These data illustrate how the power versus temperature curve uniquely identifies ethanol for a given set of conditions, and how readily this curve is distinguished from data for similar compounds such as iso-propanol and n-propanol, even under identical detection conditions.

EXAMPLE 10

Figure 20:
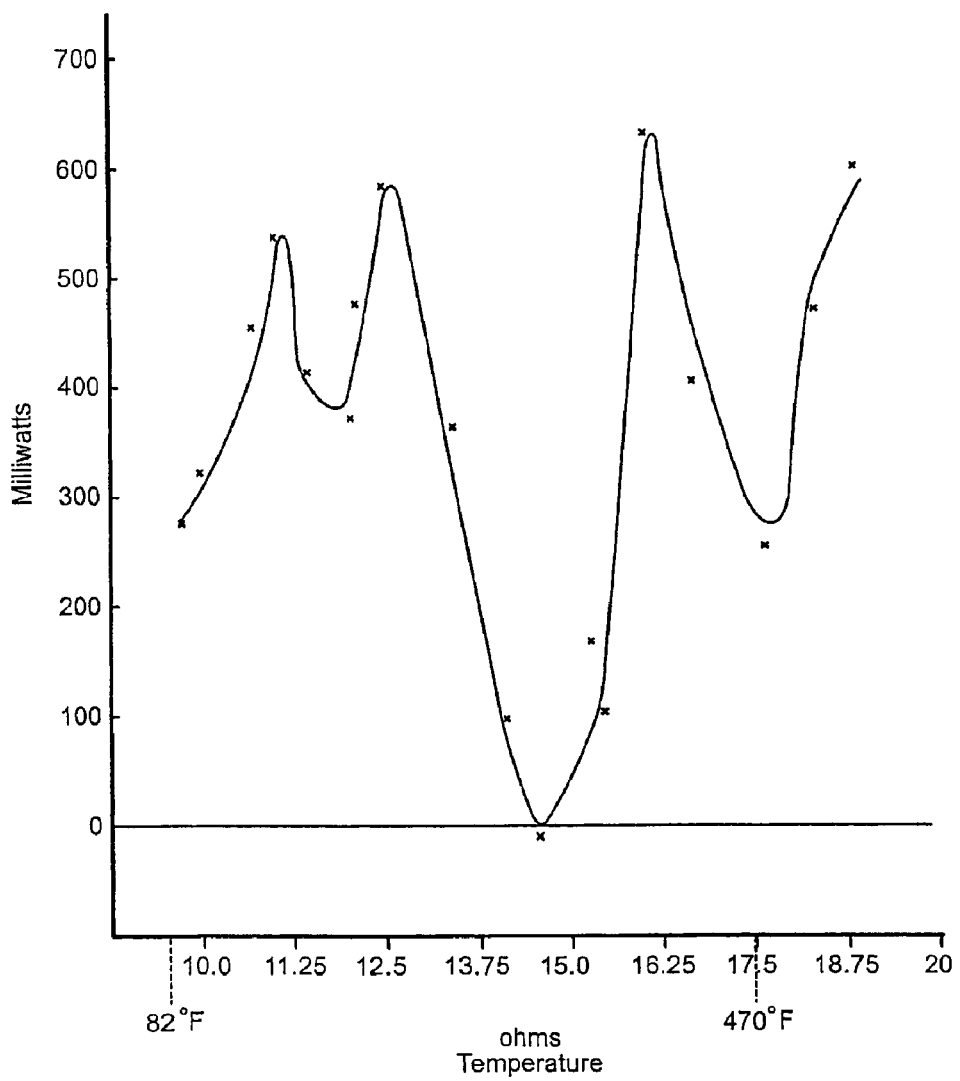
FIG. 20 is a low temperature detection plot of temperature (resistance) versus power for detecting 0.01% (vol/vol) ethanol in air in the presence of a copper oxide catalyst, at a sample gas flow rate of 2 mL/minute and an inlet gas temperature of 28° C.

Low Temperature Operation of a VRH Sensor to Detect Ethanol at a Copper Oxide Catalyst Using the protocol detailed in Examples 5 and 6, the sensor device may be used to identify and measure ethanol. FIG. 20 is a plot of power versus temperature for 0.01% (vol/vol) ethanol in air, detected in the low temperature mode using a sensing VRH coated with a copper oxide catalyst. Sample gas flow rate was 2 mL/minute, at an inlet gas temperature of temperature of 28° C. These data illustrate how the power versus temperature curve uniquely identifies a compound for a given set of conditions, and how readily this curve is distinguished from data for the same compound interacting with a different catalyst, under otherwise identical detection conditions. This distinction is a direct consequence of the differences in the energetics associated with the molecule-catalyst interaction upon varying the catalyst.

EXAMPLE 11

Construction of a Sensor Assembly for Differential Measurements

Figure 21:
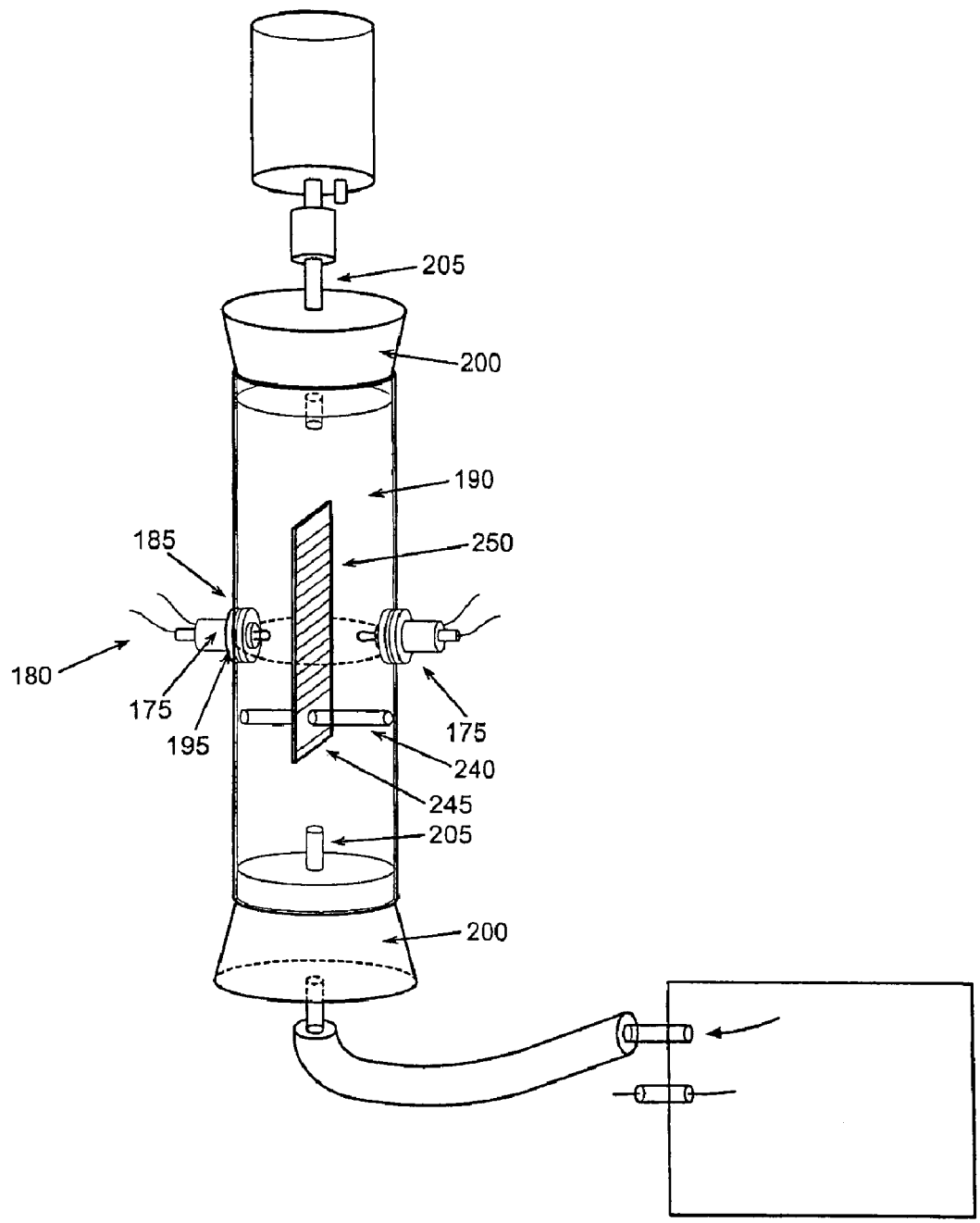
FIG. 21 illustrates one embodiment of an HTD sensor assembly of this invention, adapted for differential measurements. In this embodiment, the transducer tube contains both the HTD sensing element and the HTD reference element for simultaneous contact with the gas stream, separated by a thermal shield.

A sensor assembly adapted for differential HTD measurement operation requires the incorporation of both a sensing and a reference VRH elements in a transducer tube, as illustrated in FIG. 21. Such an assembly is constructed as follows. A glass tube 190 as described in Example 4 (Pyrex 47740 tubing; Wale Co., Inc. #BS-022), and having a notch 195 to hold the lamp-grommet assembly (175, 180, 185) as illustrated in FIG. 16, is fitted with a second notch 195, located on the side of the tube directly opposite the first notch, as shown in FIG. 21. One notch is fitted with the sensing VRH element 175, prepared as in Example 1, while the second notch is fitted with the reference VRH element 235, prepared as in Example 3. These elements are secured in a similar manner as that described for the single channel sensor assembly in Example 4.

A 1/16" copper tube 240 pierces, and is adhered with epoxy (Devon S-210-21045) to, a spruce rectangle 245. The major axis of the rectangle 245 is oriented parallel to the sides of the glass flow tube, and is coincident with the tube's center line, as illustrated in FIG. 21. Both sides of rectangle 245 are covered with a thin sheet of aluminum foil 250, which serves primarily as a thermal shield to prevent radiative heating between the sensor and reference VRH elements. The remainder of the assembly is identical to that illustrated in FIG. 16 and Example 4.

EXAMPLE 12

High Temperature Operation of a Dual Channel VRH Sensor to Detect Target Species The VRH sensor of the present invention is operated in the high temperature range to detect the presence of a target species, using the following protocol. This Example illustrates detector operation using the dual channel or differential measurement mode, in which both a sensing VRH element and a reference VRH element are employed. The sampling apparatus uses the identical physical configuration for the VRH sensor as the low temperature measurements as described in Examples 5 and 6. The VRH reference element, prepared without a catalyst, is passivated to prevent contact of the VRH with air. By connecting both sensing and reference VRH elements using the Anderson loop measurement circuit topology as described in IEEE Instrumentation & Measurement Magazine 1998, vol. 1 (no. 1), pages 6-15 and U.S. Pat. No. 5,371,469 (both incorporated herein by reference) and using the differential measurement mode, the output voltage signal requires no further data processing to remove the primary systematic errors from the data.

A typical high temperature measurement test was conducted in a substantially similar manner as that used in the low temperature test described in Example 5. Note that either single HTD or differential HTD operation may be used in either low temperature or high temperature ranges. In this example, high temperature-differential HTD operation employed the Anderson Loop amplification circuitry to connect the sensing and reference VRH elements. During operation of the sensor, the temperature of the coils was measured using an IR detector (Infrared Thermometer #U-39800-02, Cole-Palmer Instrument Co.).

In a typical detection test, a known amount of a liquid or gas sample, which has been calculated to achieve a known molecular concentration after vaporization of the liquid or complete mixing of the gas, is added to the container of known volume. In the case of a liquid, the sample container is shaken for about 30 seconds, then allowed to stand for about 1 hour to permit complete vaporization of the liquid. A heating pad can be used to gently heat the container to aid in vaporization of the liquid, and in raising and regulating sample gas temperature, in which case thermal equilibration also occurs during this one hour period as well.

The temperature of the gas is measured, the vacuum pump is activated, and a slow gas flow (around 1 mL/min) is initiated. Gas flow continued for about 50-60 seconds prior to starting detection, to ensure a constant target molecule concentration throughout the gas flow path. For dual channel operation, only a single scan is required, and no baseline scan or subtraction of the baseline (air only) scan data are required.

EXAMPLE 13

Data Processing for Differential Operation of the VRH Sensor

The parameters recorded using the offset strategy during a differential, high temperature run are as follows. The resistance (which is proportional to temperature) across the reference VRH versus sensor VRH is electrically varied. A plot of resistance on the X-axis is also proportional to the temperature of the VRHs. Upon reaction, energy transfer between the catalytic surface and the target molecule occurs, and the VRH is catalytically heated for an exothermic process. Sensor VRH heating causes a resistance increase in the circuit, which is proportional to the temperature change due to the reaction, which in turn is directly related to the molecular concentration of the target species being consumed.

Voltage, being directly proportional to resistance, increases with temperature; thus the magnitude of voltage measured from the circuit is directly related to the molecular concentration of the molecule of interest in the sample gas stream. A plot of resistance versus voltage (Y-axis) allows the determination of a specific molecule along with its concentration at a given flow rate of gas. The gas flow was monitored using the instrumentation outlined in Example 5. Voltage maximum versus the corresponding catalyst temperature is the identification information for a given concentration of a molecule at a given sample gas flow rate.

The collection of data for voltage, current, catalyst, target molecule, gas flow rate, and the like uniquely identify the specific target molecule. The efficiency of the excitation process will differ from catalyst to catalyst, therefore the voltage maximum for a given temperature will vary with the specific catalyst employed. Therefore using another catalyst will give a different voltage response at a different temperature for a specific molecule and flow rate, if that different catalyst induces reaction at all. This selectivity property is useful in that different catalysts may be used to resolve or separate various mixtures of different target molecules.

EXAMPLE 14

Figure 22:
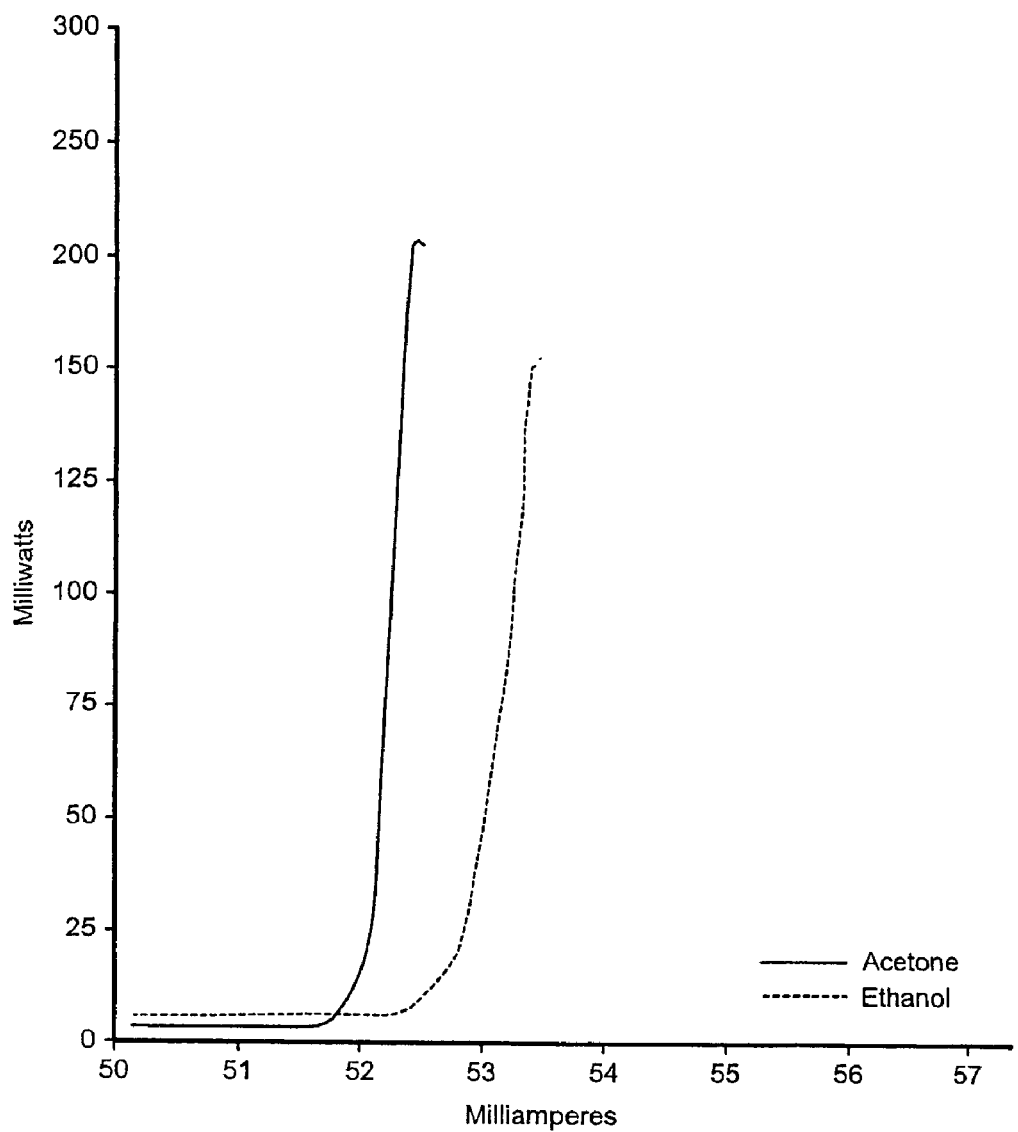
FIG. 22 is a high temperature differential scan of current (mA) versus potential (mV) for 0.01% (vol/vol) ethanol and 0.01% (vol/vol) acetone in air in the presence of a copper oxide catalyst, at a sample gas flow rate of 2 mL/minute and an inlet gas temperature of temperature of 28° C.

High Temperature Operation of a VRH Sensor to Detect Ethanol and Acetone at a Copper Oxide Catalyst Using the protocol detailed in Examples 12 and 13, the sensor device may be used to identify and measure ethanol and acetone. FIG. 22 is a high temperature differential scan of current (ma) versus potential (mV) for 0.01% (vol/vol) ethanol and 0.01% (vol/vol) acetone in air, detected in the high temperature mode using a VRH coated with a copper oxide catalyst as in Example 2. Sample gas flow rate was 2 mL/minute, at an inlet gas temperature of temperature of 28° C.

FIG. 22 illustrates the different temperatures required for oxidation of the two different compounds, demonstrating the reactive ability of copper oxide in discriminating between these two compounds. In order to avoid confusion, the two scans show only the maximum response in millivolts. These data illustrate how the current which is proportional to temperature versus voltage curve uniquely identifies a compound for a given set of conditions, and how readily different compounds are distinguished even at the same catalyst, under otherwise identical detection conditions. This distinction is a direct consequence of the differences in the energetics associated with the molecule-catalyst interaction for different compounds.

EXAMPLE 15

Thermodynamic Models of Sensor Operation

To more fully understand the requirements to be satisfied by the signal conditioning electronics used to operate the sensor assembly of this invention, thermodynamic models of sensor operation, in terms of an electrical circuit paradigm, are provided in FIGS. 14 and 15. FIG. 14 illustrates an electrical circuit analog of the sensor assembly thermodynamics in which the sensing VRH and the reference VRH exist on separate bodies, separated by a radiation shield. FIG. 15 illustrates electrical circuit analog of the thermodynamics of the sensor assembly in which the catalyst-coated sensing VRH and the reference VRH are situated on the same body.

Abbreviations. The signal conditioning electronics are called upon to perform tasks that include monitoring heat flow and temperature, which may be understood thermodynamically in terms of the electrical component analogy in FIGS. 14 and 15, using the following abbreviations. Different units may be used in any of these quantities, as long as the units for all calculations are internally consistent.

$C$=Thermal capacity, $C=Q/° C$.
$C_{CF}$=Thermal capacity of the catalyst face
$G$=Gauge factor for a sensor HTD, catalytic energy flow rate at $T_c$ per unit target gas concentration in Watts/(mole/liter)
$K$=Calibration factor for the offset measurement strategy, target gas gram molecular weight per liter of target gas concentration (mole/liter) per ° C. of temperature difference between a sensor HTD and a reference HTD, (mole/liter)/° C.
$P$=Power, due either to thermal or electrical energy flow rate in Joules/sec or Watts, $P=Q/t$
$P_C$=Catalytic power applied to a sensor HTD in Watts
$P_L$=Catalytic power developed at the target molecule concentration x at zero thermal margin
$P_N$=Catalytic power uncertainty representing the measurement noise level
$P_R$=Non-catalytic thermal power applied to a reference HTD, typically electrical power in Watts
$P_S$=Non-catalytic thermal power applied to a sensor HTD, typically electrical power in Watts
$\Delta P_S$=Instantaneous difference between the non-catalytic thermal power applied to a sensor HTD and non-catalytic thermal power applied to a reference HTD positioned in the same sample gas
$Q$=Energy, either thermal or electrical, Joules
$R$=Thermal resistance, $R=° C./W$
$R_C$=Total thermal resistance from the catalytic surface of an HTD to its ambient temperature
$R_{CF}$=Thermal conduction resistance from the catalytic surface of an HTD to its face capacity
$R_N$=Thermal resistance variations (noise) from the face of an HTD to its environment
$T$=Temperature in ° C.
$\Delta T$=Temperature change in ° C.
$T_1$=Temperature of a heat source
$T_2$=Temperature of a heat sink
$T_B$=Temperature at the body of an HTD
$T_C$=Temperature at which catalytic heat flow is to be observed
$T_G$=Temperature of sample gas to which heat transfer from an HTD takes place by convection
$T_H$=Temperature of the HTD holder to which heat transfer from an HTD takes place by conduction
$T_M$=Thermal margin, the maximum usable $\Delta T$ when using non-catalytic power to control the temperature of an HTD.
$T_R$=Temperature at which reference beat flow is to be observed, substantially equal to $T_C$ for null-balance measurements, will differ from $T_C$ for offset measurements
$T_S$=Temperature at which sensor heat flow is to be observed, substantially equal to $T_C$ for null-balance measurements, may differ from $T_C$ for offset measurements
$T_W$=Temperature of the wall to which heat transfer from an HTD takes place by radiation
$x$=Concentration of the molecule to be identified in moles/liter
$\Delta x$=Change in concentration of the molecule to be identified
$x_L$=Saturation limit concentration of the molecule to be identified
$\Delta x_L$=Change in saturation limit concentration due to a $\Delta x$ transient The signal conditioning electronics provide a measurement of target molecule concentration from the change in power required to maintain the sensor HTD at substantially the desired instantaneous temperature, as detailed below.

Catalytic Heat Flow. $P_C$ represents the rate of catalytic heat flow developed at the catalyst of a sensor HTD by the presence of a certain concentration of gas, x, at the temperature at which catalytic heat flow is to be observed, $T_C$. For a given HTD, the available surface area of catalyst, among other things, determines the catalytic heat flow which is developed at $T_C$.

G is defined as the gauge factor (or sensitivity) of an HTD. G is the catalytic heat flow developed at the catalyst of a sensor HTD per unit concentration of the target molecule in a gas sample, usually gram molecular weight/liter of concentration. A sensor HTD will have a substantial magnitude of G and, by design, a reference HTD will have a G of essentially zero.

$$G=P_C/x$$

G assumes a positive value for exothermic catalytic activity and a negative value for endothermic catalytic activity.

The plot of G vs. $T_C$ over a range of temperature operation is a pattern which can be used to identify the presence and concentration of a particular target gas in a sample gas. In some cases the maximum or minimum value of G occurs at a temperature unique for a given catalyst and only one target molecule. In such cases detector operation at substantially the desired instantaneous temperature will specifically identify a target gas.

Concentration Measurements. The concentration of a target molecule, x, is estimated in a null-balance measurement by observing the change in non-catalytic power, $\Delta P_S$, that is required to maintain a sensor HTD at the desired temperature, $T_C$, in the presence of catalytic power, $P_C$, that operates to change the temperature of the sensor HTD.

$$x=\Delta P_S/G$$

$$x=P_C/G$$

The measurement described above is commonly termed a "single-ended" measurement and care must be exercised to avoid variations in ambient conditions that might affect and thereby contaminate the measurement results. As a result, uncertainties due to variations in ambient conditions are typically reduced by using "differential" measurements, where the instantaneous difference between the non-catalytic thermal power applied to a sensor HTD, and non-catalytic thermal power applied to a reference HTD is observed, as follows.

$$\Delta P_S=P_S-P_R$$

$$x=(P_S-P_R)/G$$

The concentration of a target molecule, x, is estimated in a single-ended offset measurement by observing the change in temperature, $\Delta T$, that develops at a sensor HTD due to $P_S$, which operates to change the temperature of the sensor HTD. A calibration factor, K, relates the temperature change of the sensor HTD to the change in concentration of a target molecule in a sample gas.

$$x=K\Delta T$$

The concentration of a target molecule, x, is estimated in a differential offset measurement by observing the difference in temperature, $\Delta T$, that develops between a sensor HTD due to $P_S$ which operates to change the sensor HTD temperature, and a reference HTD that tends not to change in temperature due to variations in x.

$$\Delta T=(T_S-T_R)$$

The magnitude of K is determined by a calibration specific to a particular detector and measurement strategy and non-catalytic energy control strategy.

The typical offset measurement approach implements a sensor VRH and a reference VRH operated using the Anderson loop measurement circuit topology with excitation level under closed-loop control to maintain the sensor VRH at the desired temperature, $T_C$. The Anderson loop measurement circuit topology is described in U.S. Pat. No. 5,371,469, the entirety of which is incorporated herein by reference and in IEEE Instrumentation & Measurement Magazine 1998, vol. 1 (no. 1), pages 6-15.

Thermal Margin. Thermal margin, $T_M$, is defined as the difference between the temperature at which catalytic heat flow is to be observed and the ambient temperature to which heat flows from an HTD. It is the maximum temperature change available by means of decreasing the non-catalytic energy input to an HTD, and is an important factor in assessing the likelihood of thermal saturation, as described below.

$$T_M=T_C-T_A$$

The observation of catalytic reactions that tend to increase the magnitude of $T_M$ tends to decrease the non-catalytic heat energy required to maintain the temperature of an HTD at $T_C$.

Electrical power dissipation is typically used to provide the non-catalytic heat energy when a variable resistance heater (VRH) is the means for providing non-catalytic heat energy to an HTD. Since electrical resistance can only dissipate power due to electrical current flow, a VRH becomes unable to maintain the desired temperature at $T_C$ when negative electrical power dissipation (cooling rather that heating) becomes required to achieve control.

$T_M$ represents the maximum usable $\Delta T$ for a particular test temperature condition, $T_C$, in which additional non-catalytic energy flow tends to decrease the magnitude of $T_M$ in null-balance measurements. When using non-catalytic power to control the temperature of an HTD, $T_M$ identifies the risk of being unable to control the temperature of an HTD to be $T_C$ because non-catalytic cooling may become required.

Thermal Resistance. Thermal resistance, R, is the ratio of the difference in temperature between a heat source at temperature $T_1$, and a heat sink at temperature $T_2$, and the heat flow per second (thermal power) that results from this temperature difference.

$$R=(T_1-T_2)/P$$

The total effective thermal resistance from the catalytic surface of an HTD to the environment in which the HTD is operating is $R_C$. It includes beat transfer by all available means, including any means of conduction, convection and radiation. $R_C$ can be estimated from measurements during steady-state conditions of the VRH temperature, for example $T_C$, the ambient temperature, for example $T_G$, and non-catalytic power, for example $P_C$. $R_C$ an be readily calculated from thermodynamic models after the various thermal resistance components have been estimated.

The various internal thermal resistances and capacities are estimated from measurements during various transient temperature conditions. The time constants of the exponential rises and falls of temperature can be used to identify the parameters that model an HTDs thermodynamics. Standard parameter estimation software can also be employed for this purpose.

Maximum Concentration Measurement Due to Thermal Margin. For steady state operation (constant temperature), the maximum concentration of the target molecule that can be observed using the null-balance measurement strategy is limited by several factors, including thermal margin ($T_M$), total thermal resistance from the catalytic surface of an HTD to its ambient temperature ($R_C$), gauge factor (G), and target molecule concentration, (x), and the like. Given that $$T_M=P_C/R_C,$$

and substituting $P_C=G\,x$ and setting $x=x_L$, the target molecule concentration that results in thermal saturation $$T_M=G\,x_L/R_C.$$

Solving for $x_L$ $$x_L=(T_M R_C)/G$$

The above equation calculates the maximum concentration of the target molecule in a gas sample that may be observed by a particular sensor HTD. In practice, a factor of safety is used to deal with uncertainties in the level of and changes expected in the concentration of the target molecule and also to deal with the possibility that a molecule concentration from other than the target gas may cause some catalytic heat flow.

Thermal Capacity. Heat energy is stored in the heat capacity, C, of all parts of an HTD as temperature changes, $\Delta T$, occur in the HTD.

$$C=Q/\Delta T$$

Thermal resistance and heat capacity are distributed (existing uniformly throughout the material surface area or volume) parameters, however useful thermodynamic models of an HTD can be constructed using lumped (single component representations of a segment of the overall surface area or volume) parameters. The thermal models of a sensor with catalyst and reference VRHs on separate bodies as demonstrated in FIG. 14, and on the same body, as demonstrated in FIG. 15, which follow are simple lumped parameter models.

The product of R and C has the units of time, t, and represents the time required, after a step change in heat input, to reach 63% of the steady state temperature distribution (the typical definition of a time constant). C is ignored for steady state calculations (constant temperature) and included in dynamic calculations (variable temperature).

Transient Conditions. For sudden (t<<RC) changes in target gas concentration x, transient thermal saturation is reached at lower concentrations than for steady state concentrations because lower thermal resistances and capacities predominate. In the thermodynamic models presented here and in FIGS. 14 and 15, the catalyst face skin thermal resistance $R_{CF}$ and capacity $C_{CF}$ predominate. The so-called "face skin" region models a region of an HTD consisting of the outer surface of the catalyst itself and to a small depth beneath the catalyst that is modeled to predict rapid transient behavior. A sudden increase in target gas concentration will raise the HTD's face skin temperature before the majority of the HTD begins to heat up. For nearly instantaneous changes in concentration, the skin temperature (at a small depth from the surface) remains momentarily at essentially the previous $T_C$ but the concentration which results in thermal saturation, $x_L$, decreases by $\Delta x_L$.

$$\Delta x_L = (T_M R_{CF})/G$$

$R_{CF}$ will be lower than $R_C$. If the initial value of $x_L$ is zero concentration, $\Delta x_L$ required to achieve transient thermal saturation will be significantly less than $x_L$ for steady-state thermal saturation.

Signal-to-Noise Ratio. There will be some variation in $P_C$ observed under normal system operation conditions. Variations in the environment of an HTD create these variations in $P_C$ measurements and thereby induce uncertainties in observations. These variations are likely due primarily to variations and turbulence in the flow of the sample gas in the vicinity of an HTD, which causes variations in the convection of heat between an HTD and the sample gas. These variations can be represented by $R_N$ which represents the effective thermal resistance change responsible for noise in measurements. This analog component is not included in the Figures.

Noise analysis in terms of $R_N$ is the preferred modeling approach for random variations in the output because the uncertainty caused by random variations in $x_L$ is typically much less than the random variations in R due to turbulence in the flow of the sample gas. $R_N$ predominately establishes the system noise floor and thereby the overall precision of sample gas concentration measurement.

We define signal-to-noise ratio, SNR, as the ratio of the maximum available signal within the thermal margin, $P_L$, to the measurement signal noise floor, $P_N$, as follows.

$$SNR = P_L/P_N = (G x_L/R_C)/(G x_L/R_N)$$

$$SNR = R_N/R_C$$

It is possible to improve signal-to-noise performance through lowering the measurement noise floor by reducing sample gas flow variations and turbulence. This can be achieved by simply turning off the sample gas pump momentarily during measurement intervals. This is a practical noise reduction method whenever the sample gas concentration would be minimally affected by catalytic action while the sample gas pump is turned off during the measurement interval.

All of the publications or patents mentioned herein are hereby incorporated by reference in their entireties. The above examples are merely demonstrative of the present invention, and are not intended to limit the scope of the appended claims.

What is claimed is:

1. A sensor for detecting gas phase substances, comprising:
   a sensing element in contact with the gas phase substances, comprising:
   a first resistance temperature detector which functions as a temperature detector and a variable resistance heater, and
   a first catalyst in thermal contact with the first resistance temperature detector, wherein the first catalyst interacts with the gas phase substances;
   a reference element in contact with the gas phase substances, comprising:
   a second resistance temperature detector which functions as a temperature detector and a variable resistance heater, and
   a second catalyst in thermal contact with the second resistance temperature detector, wherein the second catalyst interacts with the gas phase substances;
   a thermal barrier separating the sensing element from the reference element; and
   a heat flow monitor connected to both the sensing and reference elements for measuring any change in heat flow for the sensing element relative to the reference element by monitoring the change in electric power needed to maintain the first resistance temperature detector at a desired temperature relative to the second resistance temperature detector.

2. The sensor of claim 1, wherein the interaction between the first and second catalyst and the gas phase substances comprises one of endothermic and exothermic heat flow from the first and second catalyst to the first resistance temperature detector.

3. The sensor of claim 1, wherein the first catalyst comprises a first catalyst face of a catalyst crystal and the second catalyst comprises a second catalyst face of the catalyst crystal.

4. The sensor of claim 3, wherein the catalyst crystal is an oxide catalyst.

5. The sensor of claim 4, wherein the oxide catalyst is selected from a metal oxide, boride, carbide, silicide, nitride, phosphide, arsenide, sulfide, selenide, telluride, fluoride, chloride, bromide, or iodide; a non-metal oxide, boride, carbide, suicide, nitride, phosphide, arsenide, sulfide, selenide, telluride, fluoride, chloride, bromide, or iodide; a metal; an alloy, a substance in which more than one metal or more than one nonmetal are combined with an element; a substance in which a metal or a non-metal are combined with more than one other element; or a combination thereof.

6. The sensor of claim 1, wherein the heat flow monitor comprises an Anderson Loop measurement circuit topology.

7. The sensor of claim 1, wherein the heat flow monitor comprises a Wheatstone bridge measurement circuit topology.

8. The sensor of claim 1, wherein the heat flow monitor comprises a Kelvin circuit topology.

9. The sensor of claim 1, wherein the first and second temperature detectors comprise a material selected from nickel, platinum, or tungsten.

* * * * *